(12) United States Patent
Vogt et al.

(10) Patent No.: US 7,118,915 B2
(45) Date of Patent: Oct. 10, 2006

(54) MUTEINS OF APOLIPOPROTEIN D

(75) Inventors: Martin Vogt, Müchen (DE); Arne Skerra, Freising (DE)

(73) Assignee: Pieris Proteolab AG, Fresing-Weihenstephan (DE)

(*) Notice: Subject to any disclaimer, the term of this patent is extended or adjusted under 35 U.S.C. 154(b) by 95 days.

(21) Appl. No.: 10/491,001

(22) PCT Filed: Sep. 27, 2001

(86) PCT No.: PCT/EP01/11211

§ 371 (c)(1),
(2), (4) Date: Dec. 17, 2004

(87) PCT Pub. No.: WO03/029471

PCT Pub. Date: Apr. 10, 2003

(65) Prior Publication Data

US 2005/0106660 A1 May 19, 2005

(51) Int. Cl.
*C12N 15/00* (2006.01)
(52) U.S. Cl. ..................... 435/440; 435/472
(58) Field of Classification Search ............ None
See application file for complete search history.

(56) References Cited

U.S. PATENT DOCUMENTS

| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |

FOREIGN PATENT DOCUMENTS

| DE | 44 17 598 A1 | 12/1995 |
| DE | 196 41 876 A1 | 4/1998 |
| DE | 197 42 706 A1 | 4/1999 |
| DE | 199 26 068 C1 | 1/2001 |
| WO | WO 98/16873 A1 | 4/1998 |
| WO | WO 99/16873 A1 | 4/1998 |
| WO | WO 00/75308 A1 | 12/2000 |

OTHER PUBLICATIONS

Barbas, "Selection and evolution of high-affinity human anti-viral antibodies", *Trends Biotechnol.*, 1996, pp. 230-234, vol. 14 (Abstract).

Beck, et al., "Nucleotide sequence and genome organisation of filamentous bacteriophages f1 and fd", *Gene*, 1981, pp. 35-58, vol. 16.

Beste, et al., "Small antibody-like proteins with prescribed ligand specificities derived from the lipocalin fold", *Proc. Natl. Acad. Sci. USA*, 1999, pp. 1898-1903, vol. 96.

(Continued)

*Primary Examiner*—Robert A. Wax
*Assistant Examiner*—Shawn A. Hamidinia
(74) *Attorney, Agent, or Firm*—Foley & Lardner LLP

(57) ABSTRACT

A method for generating a mutein of human apolipoprotein D having detectable affinity to a given non-natural ligand of apolipoprotein D is disclosed, which comprises the steps of: (a) subjecting the apolipoprotein D to mutagenesis at the sequence positions 34 to 38, 60, 62 to 66, 68, 89 to 93, 115, 117 to 121, and 123 resulting in a plurality of muteins of apolipoprotein D; and (b) enriching resulting muteins having binding affinity for a given ligand from the plurality of muteins by selection, and/or isolating said mutein. Muteins of apolipoprotein D obtainable by this method are also disclosed.

5 Claims, 5 Drawing Sheets

OTHER PUBLICATIONS

Figure 1:
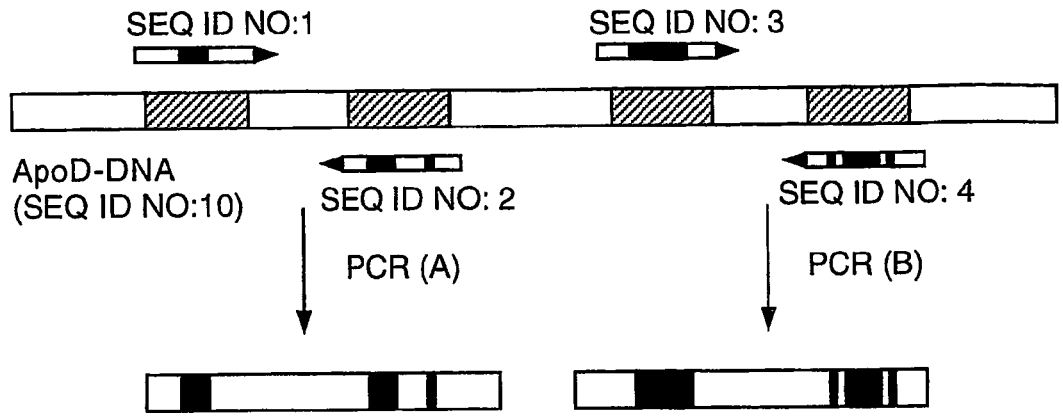
Figure 1:
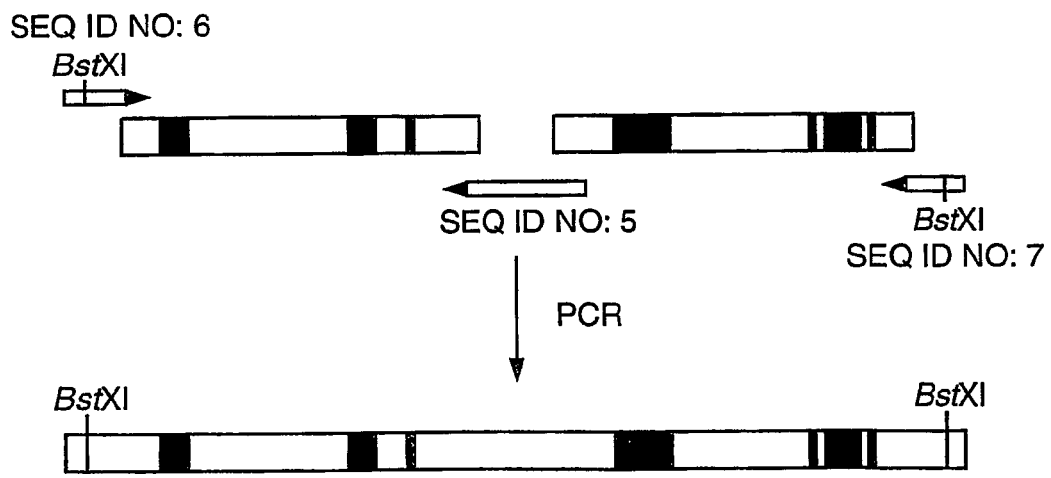

Flower, Darren R., "The lipocalin protein family : structure and function", *Biochem. J.*, 1996, pp. 1-14, vol. 318.

Fling, et al., "Peptide and protein molecular weight determination by electrophoresis using a high-molarity tris buffer system without urea", *Anal. Biochem.*, 1986, pp. 83-88, vol. 155 (Abstract).

Geisselsoder, et al., "Efficient site-directed in vitro mutagenesis", *BioTechniques*, 1987, pp. 786-791, vol. 5, No. 8 (Abstract).

Gill, et al., "Calculation of protein extinction coefficients from amino acid sequence data", *Anal. Biochem.*, 1989, pp. 319-326, vol. 182.

Hengen, Paul N., "Methods and reagents", *Trends Biochem. Sci.*, 1996, pp. 75-76, vol. 21.

Hoess, Ronald H., "Phage display of peptides and protein domains", *Current Opinion in Structural Biology*, 1993, pp. 572-579, vol. 3.

Kraulis, et al., "The serum albumin-binding domain of streptococcal protein G is a three-helical bundle: a heteronuclear NMR study", *FEBS Letters*, 1996, pp. 190-194, vol. 378.

Kunkel, et al., "Rapid and efficient site-specific mutagenesis without phenotypic selection", *Methods in Enzymology*, 1987, pp. 367-382, vol. 154 (Abstract).

Low, et al., "Mimicking Somatic Hypermutation: Affinity Maturation of Antibodies Displayed on Bacteriophage Using a Bacterial Mutator Strain", *J. Mol. Biol*, 1996, pp. 359-368, vol. 260.

Roberts, Richard W., "Totally *in vitro* protein selection using mRNA-protein fusions and ribosome display", *Current Opinion in Chemical Biology*, 1999, pp. 268-273, vol. 3.

Schlehuber, et al., "A Novel Type of Receptor Protein, Based on the Lipocalin Scaffold, with Specificity for Digoxigenin", *J. Mol. Biol.*, 2000, pp. 1105-1120, vol. 297.

Schmidt, et al., "Molecular Interaction Between the *Strep*-tag Affinity Peptide and its Cognate Target, Streptavidin", *J. Mol. Biol.*, 1996, pp. 753-766, vol. 255.

Skerra, et al., "Filter screening of antibody Fab fragments secreted from individual bacterial colonies: specific detection of antigen binding with a two-membrane system", *Anal. Biochem.*, 1991, pp. 151-155, vol. 196 (Abstract).

Vogt, et al., "Bacterially produced apolopoprotein D binds progesterone and arachidonic acid, but not bilirubin or E-3M2H", *Journal of Molecular Recognition*, 2001, pp.79-86, vol. 14.

Voss, et al., "Mutagenesis of a flexible loop in streptavidin leads to higher affinity for the *Strep*-tag II peptide and improved performance in recombinant protein purification", *Protein Engineering*, 1997, pp. 975-982, vol. 10, No. 8.

Wells, et al., "Rapid evolution of peptide and protein binding properties in *vitro*", *Current Opinion in Structural Biology*, 1992, pp. 597-604, vol. 2.

Yanisch-Perron, et al., "Improved M13 phage cloning vectors and host strains: nucleotide sequences of the M13mp18 and pUC19 vectors", *Gene*, 1985, pp. 103-119, vol. 33 (Abstract).

Arne Skerra, "Anitcalins':A New Class of Engineered Ligand-Binding Proteins With Antibody-Like Properties," *Molecular Biotechnology*, Jun. 2001, pp. 257-275, vol. 74, XP001079016.

D. Flower, "Multiple Molecular Recognition Properties of the Lipocalin Proteinfamily," *Journal of Molecular Recognition, Heyden & Son Ltd., London, GB*, 1995, pp. 185-195, vol. 8, XP002095125.

1. PCR (A + B)

2. PCR

MUTEINS OF APOLIPOPROTEIN D

The present invention refers to a method for generating a mutein of human apolipoprotein D having detectable affinity to a given non-natural ligand of apolipoprotein D and to muteins of human apolipoprotein D obtainable by this method. The invention also refers to nucleic acids encoding such muteins, a pharmaceutical composition comprising a mutein of the invention as well as to various uses of the mutein of human apolipoprotein D.

Human apolipoprotein D (ApoD) is a functionally important member of the lipocalin family of proteins (for a review, see Flower, Biochem. J. 318, (1996) 1–14). Although it is involved in serum lipid transport and is abundant in various tissues, its precise physiological role has remained a matter of speculation up to now. Recent studies show that the recombinant protein specifically binds progesterone and arachidonic acid, both in the 1 μm range, but not previously presumed ligands such as pregnenolone or bilinrubin and suggest that ApoD has a distinct binding specifity for low molecular weight ligands (Vogt and Skerra, J. Mol. Recognit. 14 (2001), 79–86).

Apart from its natural role, human ApoD has been of interest in studies on the production of novel proteins which can be used like immunoglobulins for the recognition and/or binding of given, non-natural ligands.

The German Offenlegungsschrift DE 197 42 706 and the PCT publication WO 99/16873 disclose the class of anticalins®; polypeptides which exhibit, similar to antibodies, specific binding characteristics for a given ligand (cf. also Beste et al., Proc. Natl. Acad. Sci. USA, 96, (1999) 1898–1903). Anticalins® are obtainable starting from polypeptides of the lipocalin family which are mutated in those four segments that correspond to the sequence positions of the linear polypeptide sequence comprising amino acid positions 28 to 45, 58 to 69, 86 to 99 and 114 to 129 of the Bilin-binding protein (Bbp). As explained in WO 99/16873 these four peptide loops include in the case of human ApoD the amino acid positions 28 to 44, 59 to 70, 85 to 98, and 113 to 127. In a preferred embodiment, WO 99/16873 teaches to mutate amino acids which correspond to sequence positions 34 to 37, 58, 60, 69, 88, 90, 93, 95, 97, 114, 116, 125, and 127 of the Bbp (cf. FIG. 1B and 3 of WO 99/16873). Correspondingly, in the case of ApoD, the sequence positions 34 to 37, 59, 61, 70, 87, 89, 92, 94, 96, 113, 115, 123, and 125 are preferred for mutagenesis in WO 99/16873.

In addition, the German patent DE 199 26 068, WO 00/75308 as well as Schlehuber et al., J. Mol. Biol. (2000), 1105–1120, describe muteins of the Bilin-binding protein such as the muteins DigA and DigA16 having specific binding activity towards the digoxigenin group. As disclosed in DE 199 26 068 and WO 00/75308 at least one of the amino acids at sequence positions 28, 31, 34 to 37, 58, 60, 69, 88, 90, 95, 97, 114, 116, 125, and 127 of Bbp is mutated in the digoxigenin-binding muteins. According to the teachings of DE 199 26 068, these positions in Bbp correspond to the sequence positions 28, 31, 34 to 37, 59, 61, 70, 87, 89, 94, 96, 113, 115, 123, and 125 of ApoD.

Though the anticalin® technology has in principle been established and presumably already yielded a promising practical application in the digoxigenin-binding Bbp muteins described above, further improvements are desirable. In view of potential pharmaceutical or therapeutic applications which anticalins® binding to tumour-specific cellular surface molecules might, for example, have, the generation of anticalins® based on the scaffold of human ApoD would be particularly desirable. Use of this protein would eliminate the need for humanisation of an lipocalin derived from Bbp subsequent to selection. Generally, a humanized anticalin® would be desirable for therapeutic applications in order to minimise an immune response.

Accordingly, it is an object of the invention to provide novel muteins of apoliprotein D having binding affinity to a given ligand.

This object is solved by the method and the muteins with the features of the independent claims.

Such a method of the invention is a method for generating a mutein of human apolipoprotein D having detectable affinity to a given non-natural ligand of apolipoprotein D comprising the steps of:
 (a) subjecting apolipoprotein D to mutagenesis at the sequence positions 34 to 38, 60, 62 to 66, 68, 89 to 93, 115, 117 to 121, and 123, resulting in a plurality of muteins of apolipoprotein D; and
 (b) enriching resulting muteins having binding affinity for a given ligand from the plurality of muteins by selection, and/or isolating said mutein.

This means that the present invention is based on the finding that muteins of ApoD having detectable affinity to a non-natural ligand can be obtained by mutagenesis, preferably, random mutagenesis of a total of 24 amino acid residues, namely the sequence positions 34 to 38, 60, 62 to 66, 68, 89 to 93, 115, 117 to 121, and 123 of ApoD. This finding is particularly surprising for the following reasons.

First, this set of sequence positions is a specific selection of the amino acid segments 28 to 44, 59 to 70, 85 to 98 and 113 to 127 which were identified in WO 98/16873 to be crucial for creating binding affinity. Only 8 residues from the 24 chosen positions according to the present invention are also included in the set of preferred positions, that are part of these segments, taught in WO 99/16873. 16 of the 24 sequence positions used in the present invention, including the complete segments of positions 62 to 66 and 117 to 121, are not comprised in the previous set.

Second, and at least of same importance, it is to be noted that a set of 24 amino acids in total is randomized, i.e. subjected to mutagenesis, in the present invention whereas a total of only 16 amino acids was mutated in WO 98/16873. When random NNS or NNK codon mutagenesis is used for the complete randomization of these 24 amino acid positions (i.e. each of the 20 natural amino acid is allowed at each of these selected 20 positions), $32^{24}$ possible codon combinations exist. If 16 amino acid positions are used for the randomization, $32^{16}$ possible codon combinations exist. Accordingly, increasing the number of amino acids which are subjected to random mutagenesis by 8 (from 16 to 24) results in an increase by $32^8 \approx 10^{12}$ in the combinatorial complexity. However, the number of mutants which can be physically realized in the corresponding DNA-based library cannot be deliberately increased due to experimental limitations and is usually restricted to a value of about $1 \cdot 10^9$ to $1 \cdot 10^{10}$ according to the state of the art. In one example of the present invention, a combinatorial DNA-based library containing just approximately $1 \cdot 10^9$ sequence variants (muteins) was used.

Considering that the small accessible section of the combinatorial sequence space is further reduced by a factor of approximately $10^{12}$, it is surprising that it is possible at all to isolate from a combinatorial library containing just $1 \cdot 10^9$ such Apo D muteins which a) do not only fold into soluble proteins but b) even have a new ligand/target specificity.

In this respect it should be noted that the approach taken here is in contrast to the teachings of WO 99/16873.

According to this reference it should be useful to maintain the total number of mutated amino acid positions within a single experiment as low as possible such that the collection of variants obtained by mutagenesis, i.e. the library, can in its totality or, at least in a representative selection therefrom, be realized as completely as possible.

It should finally be noted that it is also surprising that the present approach is successfully used for the production of a mutein having specific binding activity towards a protein epitope (cf. Example 5).

Accordingly, the present invention is also directed to a mutein of human apolipoprotein D having detectable binding affinity to a given non-natural ligand of apolipoprotein D, which is obtainable by mutagenesis of ApoD at the sequence positions 34 to 38, 60, 62 to 66, 68, 89 to 93, 115, 117 to 121, and 123.

In a preferred embodiment, the mutein of the invention carries an amino acid substitution at least at one of the sequence positions 38, 60, 62 to 66, 68, 90, 91, 93, 117 to 121 compared to apolipoprotein D. Preferably such a mutein carries an amino acid substitution at 5 to 8, more preferably at 8 to 12 of the sequence positions 38, 60, 62 to 66, 68, 90, 91, 93, 117 to 121. An ApoD mutein of this embodiment is preferred which has at least two, preferably at least three mutated amino acids at sequence positions 62 to 66 and 117 to 121 compared to the wild-type protein.

In a further embodiment a mutein of human ApoD is preferred that carries an amino acid substitution at six or more of the sequence positions 35, 37, 38, 66, 65, 66, 68, 91, 115, 119, and 123 compared with apolipoprotein D.

In addition, an ApoD mutein is also preferred that carries an amino acid substitution at nine or more of the sequence positions 34 to 38, 60, 63 to 66, 68, 89 to 93, 115, 117–119 and 123 compared to apolipoprotein D.

In a further preferred embodiment, the mutein has the amino acid sequence of SEQ ID NO: 21. This mutein is also referred to as HbgA.

The muteins of the invention are able to bind the desired ligand (target) with a detectable affinity, i.e. with an affinity constant of preferably at least $10^5$ $M^{-1}$. Affinities lower than this are generally no longer measurable with common methods such as ELISA and are therefore of secondary importance for practical applications. Especially preferred are muteins which bind the desired ligand/target with an affinity of at least $10^6$ $M^{-1}$, corresponding to a dissociation constant for the complex of 1 µM. The binding affinity of a mutein to the desired target can be measured by the person skilled in the art by a multitude of methods, for example by fluorescence titration, by competition ELISA or by the technique of surface plasmon resonance. In this respect, it should be noted that besides the affinity to the given, non-natural ligand the mutein can also have a detectable binding affinity towards a natural ligand of ApoD, although specifity for the non-natural ligand might be desirable.

The ligand or target which is bound by the mutein can be any chemical moiety that, for example, can also be recognized and bound by an immunoglobulin. Accordingly, the ligand can be a chemical compound in free or conjugated form which exhibits features of an immunological hapten, a hormone such as steroid hormones or any biopolymer or fragment thereof, for example, a peptide, a protein or protein domain, a peptide, an oligodeoxynucleotide, a nucleic acid, oligo- and polysaccharides or another macromolecule or conjugates thereof. In a preferred embodiment of the invention, the target is a protein.

The muteins of the invention can have the natural amino acid sequence of ApoD outside the regions of the amino acid positions 34 to 38, 60, 62 to 66, 68, 89 to 93, 115, 117 to 121 and 123. On the other hand, the muteins disclosed here can also contain amino acid mutations outside the positions subjected to mutagenesis compared to the wild-type protein as long as those mutations do not interfere with the binding activity of the ApoD mutein. This includes that, for example, mutations, substitutions, deletions, insertion of amino acid residues as well as N- and/or C-terminal additions can be introduced into the natural amino acid sequence of ApoD.

Such modifications of the ApoD amino acid sequence within or without the selected binding region include directed mutagenesis of single amino acid positions, for example in order to simplify the subcloning of the mutated lipocalin gene or its parts by incorporating cleavage sites for certain restriction enzymes. For example, the mutations Leu23 to Pro, Pro 133 to Val and Asn 134 to Ala can be introduced in the ApoD gene in order to simplify the cloning of the mutated gene segment via two new BstXI restriction sites at these positions. Furthermore, mutations can be introduced within or without the four peptide loops in order to improve certain characteristics of the ApoD mutein, for example its folding stability or folding efficiency or its resistance to proteases. In a preferred embodiment, for instance, Cys116 is exchanged to Ser, whereby its covalent crosslinking with other proteins can be prevented and its monomeric structure can be stabilized.

The method of the present invention preferably comprises (in step (b)) (i) providing as given ligand a compound which is selected from the group consisting of a chemical compound in free or conjugated form which exhibits features of an immunological hapten, a peptide, a protein or another macromolecule, (ii) contacting the plurality of muteins with said ligand in order to allow formation of complexes between said ligand and muteins having binding affinity for said ligand, and (iii) removing muteins having no or no substantial binding affinity.

No or no substantial binding affinity means under the used conditions, no complex is formed between the ligand and the plurality of muteins which are contacted with the ligand. It is clear to the skilled man that complex formation is dependent on many factors such as concentration of the binding partners, concentration of compounds acting as competitors, ion strength of the buffers etc. The selection and enrichment is in generally carried out under conditions which will allow isolation and enrichment of muteins having an affinity constant of at least $10^5$ $M^{-1}$ to the ligand. However, the washing and elution steps can be carried out under varying stringency. For example, if muteins having an affinity constant of at least $10^6$ $M^{-1}$ are to be isolated, washing and elution can be performed under increased stringency, i.e. more stringent conditions. A selection with respect to the kinetic characteristics is also possible. The selection can, for instance, be performed under conditions which favor complex formation of the target with muteins that show a slow dissociation from the target (receptor), or in other words a low $k_{off}$ rate. In a preferred embodiment of the method of the invention, the selection is carried out under competitive conditions.

The term "plurality" as used herein means that at least two muteins that differ from each other in their amino acid sequences are present. The upper limit of muteins generated by mutagenesis is usually restricted by the experimental conditions and is generally between $10^7$ and $10^{12}$.

The term "mutagenesis" as used herein means that the experimental conditions are chosen such that the amino acid naturally occurring at a sequence position of ApoD can be substituted by at least one amino acid that is not present at this specific position in the natural polypeptide sequence. The term "mutagenesis" also includes to (additionally) modify the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of (the respective segment) of the wild-type protein. The term "random mutagenesis" means that no predetermined single amino acid (mutation) is present at a certain sequence position but that at least two amino acids can be incorporated into a selected sequence position during mutagenesis with a certain probability.

Such experimental conditions can, for example, be achieved by incorporating codons with a degenerate base composition in the structural gene of ApoD at those position which are to be mutated. For example, use of the codon NNK or NNS allows incorporation of all 20 amino acids plus the amber stop codon during mutagenesis, whereas the codon VVS limits the number of possibly incorporated amino acids to 14 since it excludes the amino acids Cys, Ile, Leu, Met, Phe, Trp, Tyr, Val from being incorporated into the selected position of the polypeptide sequence; use of the codon NMS, for example, restricts the number of possible amino acids to 11 at a selected sequence position since it excludes the amino acids Arg, Cys, Gly, Ile, Leu, Met, Phe, Trp, Val from being incorporated at a selected sequence position. In a preferred embodiment of the method of the invention, a random mutagenesis is carried out, in which at least 4, preferably 6, more preferably 8 to 12 amino acids are allowed to be incorporated into a selected sequence position of ApoD. In a particularly preferred embodiment, at least one sequence position is subjected to complete randomization, i.e. all 20 amino acids are allowed to be incorporated at this position during mutagenesis. From the above, it is also clear that the amino acid naturally present at a certain sequence position of ApoD can also be present in the mutein after having subjecting this position to mutagenesis. In a preferred embodiment of the method of the invention, the ligand is a protein. The protein can be provided either in free or conjugated form for the selection of muteins.

In a preferred embodiment of the method a nucleic acid coding for the plurality of muteins of apolipoprotein D is used, which nucleic acid results from mutagenesis, and this nucleic acid is operably fused at the 3' end with a gene coding for the coat protein pIII of a filamentous bacteriophage of the M13-family or for a fragment of this coat protein, in order to select at least one mutein for the binding of the given ligand.

For some applications, it is useful to employ the inventive ApoD mutein in a labeled form. Accordingly, the invention also refers to mutein of ApoD which is which is conjugated to a label selected from the group consisting of enzyme label, radioactive label, fluorescent label, chromogenic label, luminescent label, an hapten, biotin, metal complexes, metals and colloidal gold. The mutein can also be conjugated to an organic molecule. The term "organic molecule as used in the present application preferably means an organic molecule comprising at least two carbon atoms, but not more than 7 rotatable carbon bonds having a molecular weight between 100 and 2000 Dalton, preferably 1000 Dalton and a molecule including one or two metal atoms.

In general, it is possible to label the mutein with any appropriate chemical substance or enzyme, which directly or indirectly generates in a chemical, enzymatic or physical reaction a detectable compound or a signal that can be used for detection. An example for a physical reaction is the emission of fluorescence after excitation with radiation or the emission of X-rays by a radioactive label; alkaline phosphatase, horseradish peroxidase or β-galactosidase are examples of enzyme labels which catalyse the formation of chromogenic (colored) compounds which can then be detected. In general all labels which are used for antibodies, except those which exclusively used with the sugar moiety in the Fc part of immunoglobulins can also be used for conjugation to the muteins of the present invention. These conjugates can be prepared by means of methods known to the person skilled in the art.

One option which is particularly advantageous for practical applications of the muteins disclosed here, is the use of the muteins in the form of fusion proteins. In preferred embodiments of such a fusion protein an enzyme, a protein or a protein domain, a peptide, for example a peptide such as a signal sequence and/or an affinity tag is operably fused to the amino terminus or to the carboxy terminus of the mutein.

The fusion partner can be suitable to confer new characteristics on the mutein, for example enzymatic activity or affinity for other molecules such as proteins, macromolecules or low molecular weight targets. For example, fusions with enzymes which catalyse chromogenic or fluorogenic reactions (e.g. alkaline phosphatase, horseradish peroxidase, glutathione-S-transferase) or which can serve for the liberation of cytotoxic agents are possible. Further examples of fusion partners which can be advantageous in practice are binding domains such as the albumin-binding domain of protein G, protein A, antibody fragments, oligomerizing domains, toxins or also muteins of the invention or anticalins® with different or the same target specificity. A specific example for the latter would be a fusion protein comprising an ApoD mutein of the present invention and the digoxigenin binding mutein DigA16 disclosed in the German Patent DE 199 26 068. Affinity tags such as the Strep-Tag® or the Strep-tag® II (Schmidt et al., J. Mol. Biol. 255 (1996), 753–766) or oligohistidine tags (e.g., His6-tags) or proteins such as glutathione-S-transferase which can be used for purification by affinity chromatography and/or for detection (e.g. using the specific affinity of the Strep-tag® for streptavidin) are further examples of preferred fusion partners. Proteins with chromogenic or fluorescent properties such as the green fluorescent protein (GFP) are suitable fusion partners, too.

The term fusion protein as used herein also includes ApoD muteins of the invention, that are equipped with a signal sequence. Signal sequences at the N-terminus of a polypeptide according to the invention can be suitable to direct the polypeptide to a specific cell compartment during the biosynthesis, for example into the periplasm of *E. coli* or to the lumen of the eukaryotic cell or into the medium surrounding the cell. In so doing, the signal sequence is cleaved by a signal peptidase. It is also possible to use other targeting or signalling sequences which are necessarily located at the N-terminus of the polypeptide and which allow the localization thereof in specific cell compartments. A preferred signal sequence for secretion into the periplasm of *E. coli* is the OmpA-signal sequence. A large number of further signal sequences is known in the art.

The invention is also directed to a nucleic acid molecule comprising a sequence encoding a mutein of ApoD according to the invention or a fusion protein thereof. In a preferred embodiment the nucleic acid molecule comprises a nucleotide sequence encoding the mutein of SEQ ID NO. 21.

Since the degeneracy of the genetic code permits substitutions of certain codons by other codons which specify the same amino acid and hence give rise to the same protein, the invention is not limited to a specific nucleic acid molecule but includes all nucleic acid molecules comprising a nucleotide sequence coding for an ApoD mutein with the amino acid sequence according to the present invention.

The nucleic acid molecule comprising a nucleotide sequence encoding a mutein of ApoD as disclosed here can be operably linked to a regulatory sequence to allow expression of the nucleic acid molecule in a host cell (in vivo) or its transcription and translation in a cell-free system (in vitro).

A nucleic acid molecule such a DNA is regarded to be "capable of expressing of a nucleic acid molecule or a coding nucleotide sequence" or capable "to allow expression of a nucleotide sequence" if it contains nucleotide sequences which contain transcriptional and translational information and if such sequences are "operably linked" to nucleotide sequences which encode the polypeptide. An operable linkage is a linkage in which the regulatory DNA sequences and the DNA sequences sought to be expressed are connected in such a way as to permit gene expression. The precise nature of the regulatory regions and elements needed for gene expression may vary from organism to organism, but shall, in general, include a promoter region which, in prokaryotes for example, contains both the promoter regulatory sequence that can comprise a transcriptional region functional in a cell and a transcriptional terminating region functional in a cell. Elements used for transcription or translation are promoters, enhancers, leader sequences, transcription initiation sites and transcripton termination sites, polyadenylation signals, ribosomal binding sites such the Shine-Dalgarno sequence and the like. These regulatory sequences and/or the mutein of the invention can be part of a vector. Accordingly, the invention also refers to a vector comprising a nucleic acid sequence coding for a mutein of ApoD as disclosed here.

In a further embodiment, the invention also relates to a method for producing of a mutein of the invention or a fusion protein thereof. In this method the mutein or the fusion protein is produced starting from the nucleic acid encoding the mutein by means of genetic engineering methods in a bacterial or eukaryotic host organism and is isolated from this host organism or its culture. For this purpose a suitable host cell is usually first transformed with a vector comprising a nucleic acid molecule encoding, for instance, a NGAL mutein of the invention. The host cell, which can be any prokaryotic or eukaryotic host cell is then cultured under conditions which allow the biosynthesis of the polypeptide. The polypeptide is then usually recovered either from the cell or from the cultivation medium. Since human apolipoprotein D contains 2 structural disulfide bonds it is preferred to direct the polypeptide during a cell compartment having an oxidizing thiol/disulfide-redox milieu by use of a suitable signal sequence. Such an oxidizing milieu is present in the periplasm of bacteria such as *E. coli* or in the lumen of the endoplasm reticulum of a eukaryotic cell and usually favours the correct formation of the disulfide bonds. It is, however, also possible to produce a polypeptide of the invention in the cytosol of a host cell, preferably *E. coli*. In this case the polypeptide can, for instance, be produced in form of inclusion bodies, followed by renaturation in vitro. A further option is the use of specifically mutated strains which have an oxidizing milieu in the cytosol and thus allow allow production of the native protein in the cytosol.

As evident from the above disclosure, the mutein of the present invention or a fusion or a conjugate thereof can be employed in many applications. In general, a mutein disclosed here can be used in all applications antibodies are used in, except those with specifically rely on the glycosylation of the Fc part.

A preferred use of the mutein is the detection of a target by a mutein of the invention or a fusion protein thereof, which comprises the steps of contacting the mutein with a sample suspected of containing the given target under suitable conditions, thereby allowing formation of a complex between the mutein and the given target, and determining the complexed mutein by a suitable signal. This signal can be caused by a label such as a fluorescent or chromogenic label as explained above. This signal can also be caused by the change of a physical properties which is caused by the binding, i.e. complex formation itself. An example of such a properties is plasmon surface resonance the value of which is changed during binding of binding partners from which one is immobilized on a surface such as a gold foil.

As noted above, a mutein disclosed here and its derivatives can be employed in many areas similar to antibodies or their fragments. A mutein is preferably used for binding to a solid phase, so that the target of the mutein or a conjugate or a fusion protein of this target can be immobilized or separated. Further preferred is the use of the mutein for labelling with an enzyme, an antibody or a radioactive substance or another group with a biochemical activity or with defined binding characteristics, so that the target of the mutein or a conjugate or a fusion protein of this target can be detected or brought in contact with it. Muteins of the invention can serve for example in the detection of chemical structures by means of established bioanalytic methods such as ELISA or Western Blot, in microscopy or immunosensorics. Here, the detection signal can either be generated directly by use of a suitable mutein conjugate or fusion protein or indirectly with detection of the bound mutein by means of an antibody directed against it or for example by. using an affinity tag.

Numerous possible applications for the ApoD mutein also exist in medicine. In addition to its use in diagnostics, a mutant polypeptide of the invention which binds for example tissue- or tumour-specific cellular surface molecules can be prepared. Such a mutein can, for example, be employed in conjugated form or as a fusion protein for "tumour imaging" or directly for cancer therapy.

Another related and preferred use of a mutein described here is the target validation, i.e. the examination whether a polypeptide that is assumed to be involved in the development of a disease or disorder is indeed somehow causative of the disease or disorder. This use for validation of the protein as a pharmacological drug target takes advantage of the ability of a mutein of the present invention to specifically recognize a surface area of a protein in its native conformation, i.e. the ability of a mutein disclosed here to bind to a native epitope. In this respect, it is to be noted that this ability to bind to a native epitope has been reported only for a limited number of recombinant antibodies, irrespective whether they have been produced by the classical immunization protocol of Kohler and Milstein (Nature 256 (1975), 495–497) or by combinatorial techniques such as phage display. The use of a mutein for validation of a drug target does not only comprises the detection of a target which is a protein, but also detection of a target which is a protein domain, a peptide, a nucleic acid molecule, an organic molecule or a metal complex.

In a further aspect, the invention refers to a pharmaceutical composition comprising a mutein of apolipoprotein D according to the invention or a fusion protein thereof and a pharmaceutically acceptable carrier.

An ApoD mutein of pharmaceutical interest can, for example, be a mutein having binding to tumour-specific cellular surfaces. It can also be a mutein which binds a specific drug and which serves as a "sustained release-release" form for this drug or a long-term storage of the drug in the body of a patient. Such a mutein can be administered by any therapeutically effective route for a proteinaceous pharmaceutical, e.g. parenterally, intranasally, rectally, buccally, or by inhalation via sprays or aerosols into the respiratory tract. Administration can occur in dosage unit formulations containing conventional non-toxic pharmaceutically acceptable carriers, adjuvants and vehicles as desired. The term "parenteral" embraces delivery modes such as subcutaneous, intravenous, intramuscular, instrasternal, intra-arterial injection and infusion techniques. Due to the low molecular weight, inhalation is one of the preferred ways of administering a pharmaceutically useful mutein of the invention.

Accordingly, the ApoD mutein of the present invention can be formulated into compositions using both known pharmaceutically acceptable ingredients and methods of preparation. See, e.g., Remington et al., Pharmaceutical Sciences, 15th Ed., Mack Pub., Easton (1975).

For inhalation the muteins of the invention can be first placed into a particulate dispersed form. This can be accomplished by preparing an aqueous aerosol or solid particles which contain the respective polypeptide. Ordinarily, an aqueous aerosol is made by formulating an aqueous solution or suspension of the desired polypeptide together with conventional pharmaceutically acceptable carriers and stabilizers. The carriers and stabilizers will vary depending upon the requirements for each polypeptide, they can include nonionic surfactants (such as Tweens, Pluronics or polyethylene glycol), innocuous proteins like serum albumin, sorbitan esters, oleic acid, lecithin, amino acids such as glycine, buffers, salts, sugars or sugar alcohols. The formulations also can include bronchodilating agents. The formulations will be sterile. Aerosols generally will be prepared from isotonic solutions. The particles optionally include normal lung surfactant proteins. Exemplary formulations for inhalation of proteins are disclosed in U.S. Pat. No. 6,099,517, for example. Administration of dry powder compositions for inhalation of a mutein of the invention is also possible. Suitable dry-powder formulations are described in U.S. Pat. No. 6,123,936, for example.

One option for preparing pharmaceutical compositions suitable for inhalation includes to form aerosols of particles in an aqueous or non-aqueous, e.g. fluorocarbon propellant, suspension. Such particles include, for example, intramolecular aggregates of the polypeptides or liposomal or microcapsular-entrapped polypeptides. The aerosols should be free of lung irritants, i.e. substances which cause acute bronchoconstriction, coughing, pulmonary edema or tissue destruction. However, nonirritating absorption enhancing agents are suitable for use herein.

Suitable compositions for parenteral administration comprise pharmaceutically acceptable sterile aqueous or non aqueous solutions, dispersions, suspensions or emulsions, as well as sterile powders for reconstitution into sterile injectable solutions or into dispersions, immediately prior to use. Representative examples of suitable aqueous and non-aqueous carriers, diluents, solvents or vehicles include water, ethanol, polyols, e.g.,—glycerol, propylene glycol, polyethylene glycol—and suitable mixtures thereof, vegetable oils, e.g., olive oil, and injectable organic esters such as ethyl oleate. Fluidity may be maintained by various means including the use of coating materials such as lecithin, the maintenance of required particle size (in the case of dispersions) and surfactants.

The compositions may also contain adjuvants such as preservatives, wetting agents, emulsifying agents, dispersing agents, antibacterial and antifungal agents such as paraben, chlorobutanol, phenol and sorbic acid, isotonic agents such as sugars, sodium chloride, or agents which delay absorption such as aluminium monostearate and gelatin. The mutein may be incorporated into slow or sustained release or targeted delivery systems such as polymer matrices, liposomes and microspheres.

Injectable formulations can be sterilized by numerous means, including filtration through a bacteria-retaining filter, or by incorporating sterilizing agents in the form of sterile solid compositions which can be dissolved or dispersed in sterile water or other sterile injectable medium just prior to use.

The coding sequence for ApoD which can be obtained as described by Vogt and Skerra, J. Mol. Recognit. 14 (2001), 79–86, can serve as a starting point for mutagenesis of the peptide segments selected in the present invention. For the mutagenesis of the amino acids in the four peptide loops, the person skilled in the art has at his disposal the various known methods for site-directed mutagenesis or for mutagenesis by means of the polymerase chain reaction. The mutagenesis method can, for example, be characterized in that mixtures of synthetic oligodeoxynucleotides, which bear a degenerate base composition at the desired positions, can be used for introduction of the mutations. The use of nucleotide building blocks with reduced base pair specificity, as for example inosine, is also an option for the introduction of mutations into the chosen sequence segment or amino acid positions. The procedure for mutagenesis of ligand-binding sites is simplified as compared to antibodies, since for the apolipoprotein D only four instead of six sequence segments—corresponding to the four above cited peptide loops—have to be manipulated for this purpose. A further possibility is the so-called triplet-mutagenesis. This method uses mixtures of different nucleotide triplets each of which codes for one amino acid for the incorporation into the coding sequence One of the various applicable methods for the introduction of mutations in the region of the four peptide loops of ApoD, i.e. at sequence positions 34 to 38, 60, 62 to 66, 68, 89 to 93, 115, 117 to 121, and 123, is based on the use of four oligodeoxynucleotides, each of which is derived from one of the four corresponding sequence segments to be mutated. In the production of these oligodeoxynucleotides, the person skilled in the art can employ mixtures of nucleic acid building blocks for the synthesis of those nucleotide triplets which correspond to the amino acid positions to be mutated, so that codons or anticodons randomly arise for all amino acids or, according to the genetic code and to the composition of this mixture, for a selection of the desired amino acids at this position.

For example, the first oligodeoxynucleotide corresponds in its sequence—apart from the mutated positions—at least partially to the coding strand for the peptide loop, which is located in the polypeptide sequence of ApoD at the most N-terminal position. Accordingly, the second oligodeoxynucleotide corresponds at least partially to the non-coding strand for the second sequence segment following in the polypeptide sequence. The third oligodeoxynucleotide corresponds in turn at least partially to the coding strand for the corresponding third sequence segment. Finally, the fourth oligodeoxynucleotide corresponds at least partially to the non-coding strand for the fourth sequence segment. A polymerase chain reaction can be performed with the respective first and second oligodeoxynucleotide as well as with the respective third and fourth oligodeoxynucleotide by using the nucleic acid which codes for ApoD and/or its complementary strand as a template.

The amplification products of both of these reactions can be combined by various known methods into a nucleic acid which comprises the sequence from the first to the fourth sequence segment, and which bears the mutation at the selected amino acid position. To this end, both of the products can for example be subjected to a new polymerase chain reaction using flanking oligodeoxynucleotides as primers as well as one or more mediator nucleic acid molecules which contribute the sequence between the second and the third sequence segment. This procedure is schematically reproduced in FIG. 1. In the choice of the number of the oligodeoxynucleotides used for the mutagenesis and their arrangement within the gene sequence of the ApoD, the person skilled in the art furthermore has numerous alternatives at his disposal.

The nucleic acid molecules which code for the sequence region with the four peptide loops of ApoD and which contain mutations at the selected positions defined above can be connected by ligation with the missing 5'- and 3'-sequences of a nucleic acid coding for ApoD, and can be cloned in a known host organism. A multitude of procedures are at one's disposal for the ligation and the cloning. For example, in the course of an amplification, synthetic nucleic acid molecules with restriction endonuclease recognition sequences, which are also present at the corresponding positions in the nucleic acid sequence for ApoD, can be attached at both ends of the nucleic acid to be cloned so that a ligation is made possible following hydrolysis with the corresponding restriction enzyme. The missing 5'- and 3'-sequences of a nucleic acid coding for ApoD can also be attached to the nucleic acid molecule comprising the mutated sequence positions via PCR.

Longer sequence segments within the gene coding for ApoD can also be subjected to random mutagenesis via known methods, for example by use of the polymerase chain reaction under conditions of increased error rate, by chemical mutagenesis or by using bacterial mutator strains (Low et al., J. Mol. Biol. 260 (1996), 359–368). Such methods can also be used for the further optimization of the ligand affinity or ligand specificity of a ApoD mutein which has already been produced. Mutations which possibly occur outside the segments of the sequence positions 34 to 38, 60, 62 to 66, 68, 89 to 93, 115, 117 to 121, and 123 can often be tolerated or can even prove advantageous if they for example contribute to an improved folding efficiency or folding stability of the ApoD mutein.

After having brought the coding nucleic acid sequences subjected to mutagenesis to expression, the clones carrying the genetic information for the plurality of respective muteins which bind a given target can be selected from the library obtained. Known expression strategies and selection strategies can be employed for the selection of these clones. Methods of this kind have been described in the context of the production or the engineering of recombinant antibody fragments, such as the "phage display" technique (Hoess, Curr. Opin. Struct. Biol. 3 (1993), 572–579; Wells and Lowman, Curr. Opin. Struct. Biol. 2 (1992), 597–604) or "colony screening" methods (Skerra et al., Anal. Biochem. 196 (1991), 151–155) or "ribosome display" (Roberts, Curr. Opin. Chem. Biol. 3 (1999) 268–273).

An embodiment of the "phage display" technique (Hoess, supra; Wells and Lowman, supra; Kay et al., Phage Display of Peptides and Proteins—A Laboratory Manual (1996), Academic Press) is given here as an example of an selection method according to the invention for ApoD muteins with the desired binding characteristics. The various other possible embodiments of the "phage display" technique are hereby incorporated into the disclosure by reference. For the exemplary selection method, phasmids are produced which effect the expression of the mutated ApoD structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375–456) or fragments of this coat protein, which are incorporated into the phage coat, at the C-terminus. The C-terminal fragment ΔpIII of the phage coat protein, which contains only amino acids 217 to 406 of the natural coat protein pIII, is preferably used to produce the fusion proteins. Especially preferred is a C-terminal fragment from pIII in which the cysteine residue at position 201 is missing or is replaced by another amino acid.

The fusion protein can contain other components such as for example an affinity tag or an epitope sequence for an antibody which allows the immobilization or the later purification of the fusion protein or its parts. Furthermore, a stop codon, can be located between the region coding for ApoD (mutein) and the gene segment for the coat protein or its fragment, which stop codon, preferably an amber stop codon, is at least partially translated into an amino acid during translation in a suitable suppressor strain.

Phasmids here denote plasmids which carry the intergenetic region of a filamentous bacterial phage, such as for example M13 or f1 (Beck and Zink, Gene 16 (1981), 35–58) or a functional part thereof, so that during superinfection of the bacterial cells with a helper phage, for example M13K07, VCS-M13 or R408, one strand of the circular phasmid DNA is packaged with coat proteins and is exported into the medium as so-called phagemid. On the one hand this phagemid has the ApoD mutein encoded by the respective phasmid built into its surface as a fusion with the coat protein pIII or its fragment, wherein the signal sequence of the fusion protein is normally cleaved off. On the other hand it carries one or more copies of the native coat protein pIII from the helper phage and is thus capable of infecting a recipient generally a bacterial strain carrying an F- or F'-plasmid. In this way a physical coupling is ensured between the packaged nucleic acid carrying the genetic information for the respective ApoD mutein, and the encoded protein which is at least partially presented in functional form on the surface of the phagemid.

The vector pApoD19 (FIG. 2) can for example be used in the construction of the phasmid with the sequences coding for the ApoD muteins. The nucleic acid coding for the peptide loops can, for example, be inserted into the vector pApoD19 via both of the BstXI-restriction sites. Recombinant phasmids are incorporated by transformation into the E. coli strain, for example XL1-blue (Bullock et al., BioTechniques 5 (1987), 376–379) or TG1. In this way, clones are made which can produce many different ApoD muteins as fusion proteins.

This library, i.e. the collection of the clones obtained, is subsequently superinfected in liquid culture according to known methods with an M13-helper phage. After this infection the incubation temperature of the culture can be reduced for production of the phagemids. Preferred incubation temperatures are those in which the optimal folding of the ApoD mutein as a component of the fusion protein with the phage coat protein or its fragment is expected. During or after the infection phase the expression of the gene for the fusion protein with the ApoD mutein can be induced in the bacterial cells. The induction conditions are chosen such that a substantial fraction of the phagemids produced presents at least one ApoD mutein. The phagemids are isolated after a culture incubation phase of for example 6 to 8 hours. Various methods are known for isolation of the phagemids, such as for example precipitation with polyethylene glycol.

The isolated phasmids can be subjected to a selection by incubation with the desired ligand, wherein the ligand is present in a form allowing at least a temporary immobilization of those phagemids carrying muteins with the desired binding activity as fusion proteins in their coat. Among the various embodiments known to the person skilled in the art, the ligand can for example be conjugated with a carrier protein such as serum albumin and be bound via this carrier protein to a protein binding surface, for example polystyrene. Microtiter plates suitable for ELISA techniques or so-called "immuno-sticks" can preferably be used for this immobilization of the ligand. Alternatively, conjugates of the ligand can also be implemented with other binding groups such as for example biotin. The ligand can then be immobilized on surfaces which selectively bind this group, such as for example microtiter plates or paramagnetic particles coated with streptavidin or avidin.

Residual protein- or phagemid-binding sites present on the surfaces which are charged with targets can be saturated with blocking solutions known for ELISA-methods. The phagemids are for example subsequently brought in contact in a physiological buffer with the target immobilized on the surface. Unbound phagemids are removed by multiple washings. The phagemid particles remaining on the surface are subsequently eluted. For elution, the free target can be added as a solution. But the phagemids can also be eluted by addition of proteases or, for example, in the presence of acids, bases, detergents or chaotropic salts, or under moderately denaturing conditions. A preferred method is the elution using buffers of pH 2.2, wherein the eluate is subsequently neutralized.

Afterwards, E. coli cells are infected with the eluted phagemids using generally known methods. The nucleic acids can also be extracted from the eluted phagemids and be incorporated into the cells in another manner. Starting from the E. coli clones obtained in this way, phagemids are in turn generated by superinfection with M13-helper phages according to the method described above and the phagemids propagated in this way are once again subjected to a selection on the surface with the immobilized ligand. Multiple selection cycles are often necessary in order to obtain the phagemids with the ApoD muteins in enriched form. The number of selection cycles is preferably chosen so that in the subsequent functional analysis at least 0.1% of the clones studied produce ApoD muteins with detectable or detectable affinity for the given ligand. Depending on the size, i.e. the complexity, of the library employed, 2 to 8 cycles are typically required to this end.

For the functional analysis of the selected muteins, an E. coli strain is infected with the phagemids obtained from the selection cycles and the corresponding double stranded phasmid DNA is isolated. Starting from this phasmid DNA or also from the single-stranded DNA extracted from the phagemids, the nucleic acid sequences of the selected lipocalin muteins can be determined by the methods common for this purpose and the amino acid sequence can be derived therefrom. The mutated region or the sequence of the entire ApoD mutein can be subcloned in another expression vector and expressed in a suitable host organism.

pApoD10 can for example be used as the expression vector (cf. FIG. 3) and the expression with pApoD10 derivatives can be performed in E. coli strains, for example E. coli-TG1. The ApoD muteins produced by genetic engineering can be purified by various proteinchemical methods. The ApoD muteins produced for example with pApo10 or pApoD12 carry the affinity peptide Strep-Tag II (Schmidt et al., J. Mol. Biol. 255 (1996), 753–766) at their C-terminus and can therefore preferably be purified by streptavidin affinity chromatography.

The selection can also be carried out by means of other methods. Many corresponding embodiments are known to the person skilled in the art or are described in the literature. A combination of methods can also be applied. For example, clones selected or at least enriched by "phage display" can additionally be subjected to a "colony screening". This procedure has the advantage that individual clones can directly be isolated with respect to the production of an ApoD mutein with detectable binding affinity for a ligand.

In addition to the use of E. coli as host organism in the "phage display" technique or the "colony screening" method, other bacterial strains, yeast or also insect cells or mammalian cells can for example be used for this purpose. In addition to the selection of an ApoD mutein from a primary library produced starting from a coding nucleic acid sequence for a mutein, comparable methods can also be applied in order to optimize a mutein with respect to the affinity or specificity for the desired ligand by repeated, optionally limited mutagenesis of its coding nucleic acid sequence.

It is surprising that by use of the method of the invention ApoD muteins can be isolated which show high affinity to a given ligand. A binding constant of more than $10^6$ $M^{-1}$ was determined for hemoglobin with one of the muteins described in the examples. This affinity value is of the same order of magnitude as the affinity of ApoD to its possible natural ligands progesterone and arachidonic acid (Vogt & Skerra, J. Mol. Recognit. 14 (2001), 79–86). Moreover, hemoglobin bears no structural relationship whatsoever to progesterone or arachidonic acid.

It is also possible to attain affinities for given ligands with the ApoD mutein that are comparable with the affinities which are known for antibodies from the secondary immune response. It is additionally possible to subject the ApoD muteins produced to a further, optionally partial random mutagenesis in order to select variants of even higher affinity from the new library thus obtained. Corresponding procedures have already been described for the case of recombinant antibody fragments for the purpose of an "affinity maturation" (Low et al., supra; Barbas and Burton, Trends Biotechnol. 14 (1996), 230–234) and can also be applied to an ApoD mutein disclosed here in a corresponding manner by the person skilled in the art.

Figure 2:
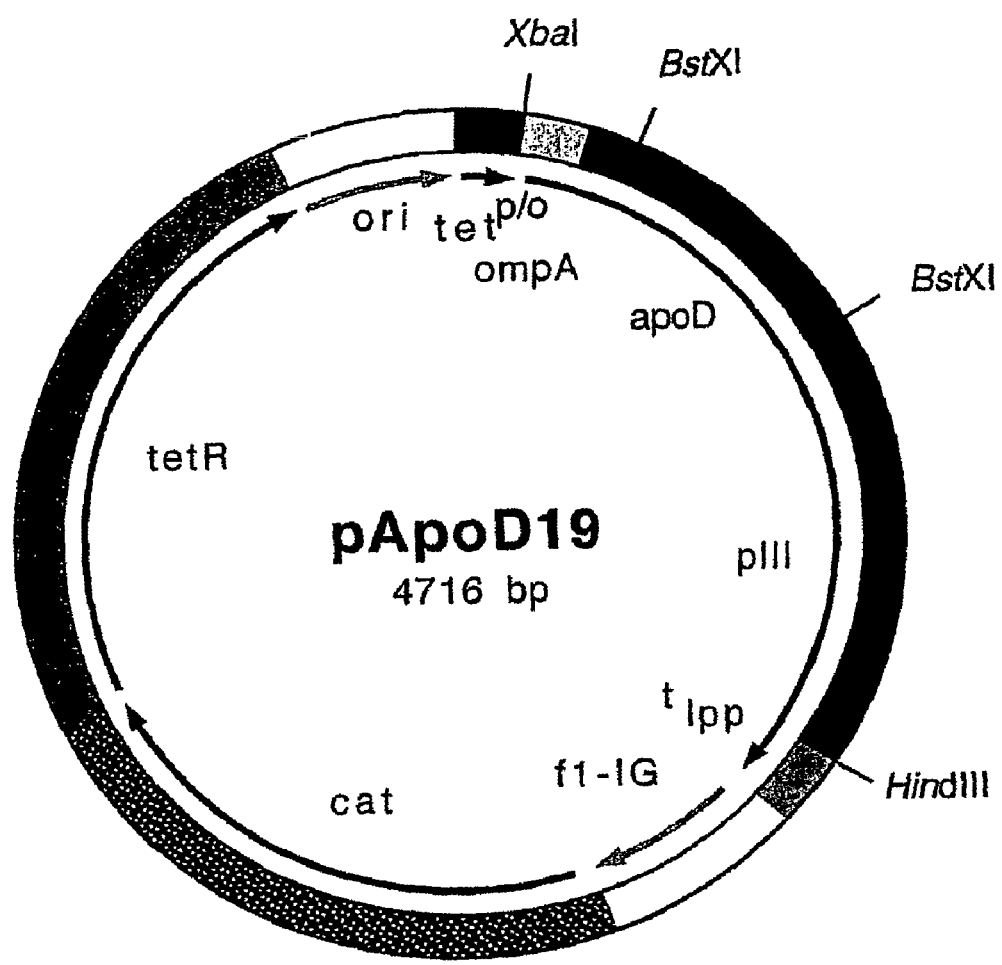
Figure 3A:
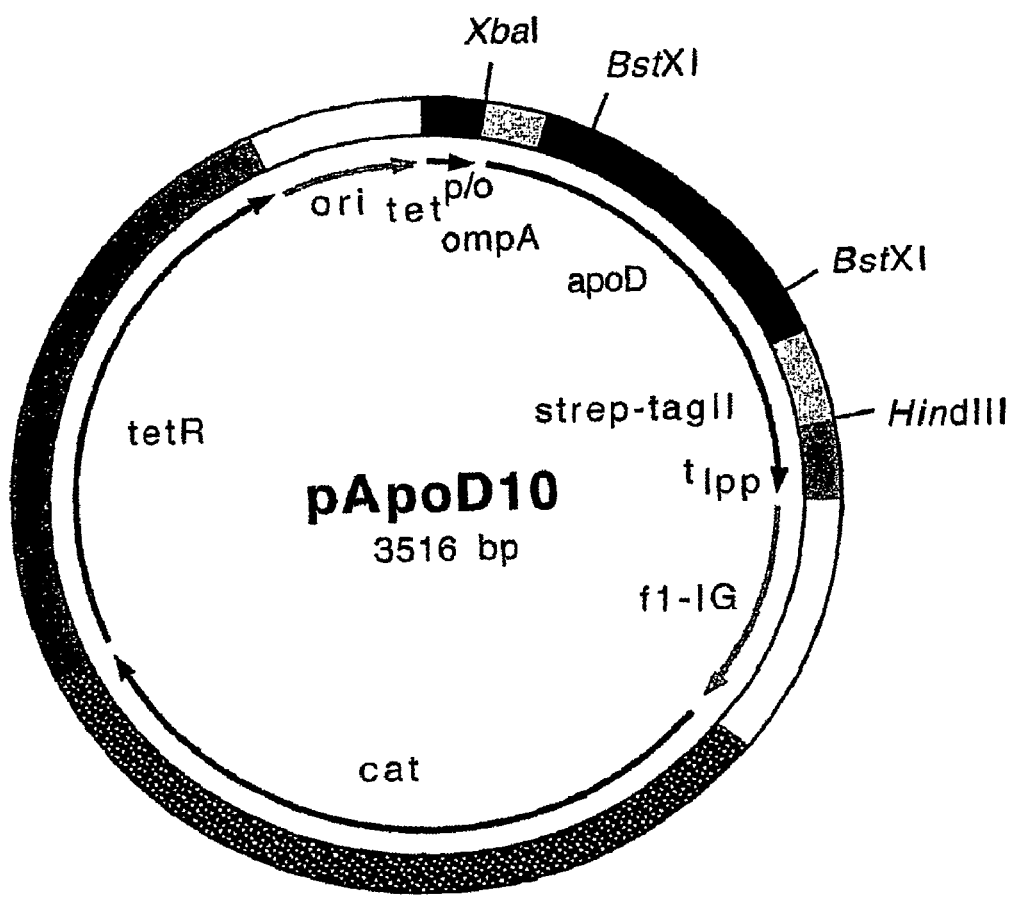
Figure 3B:
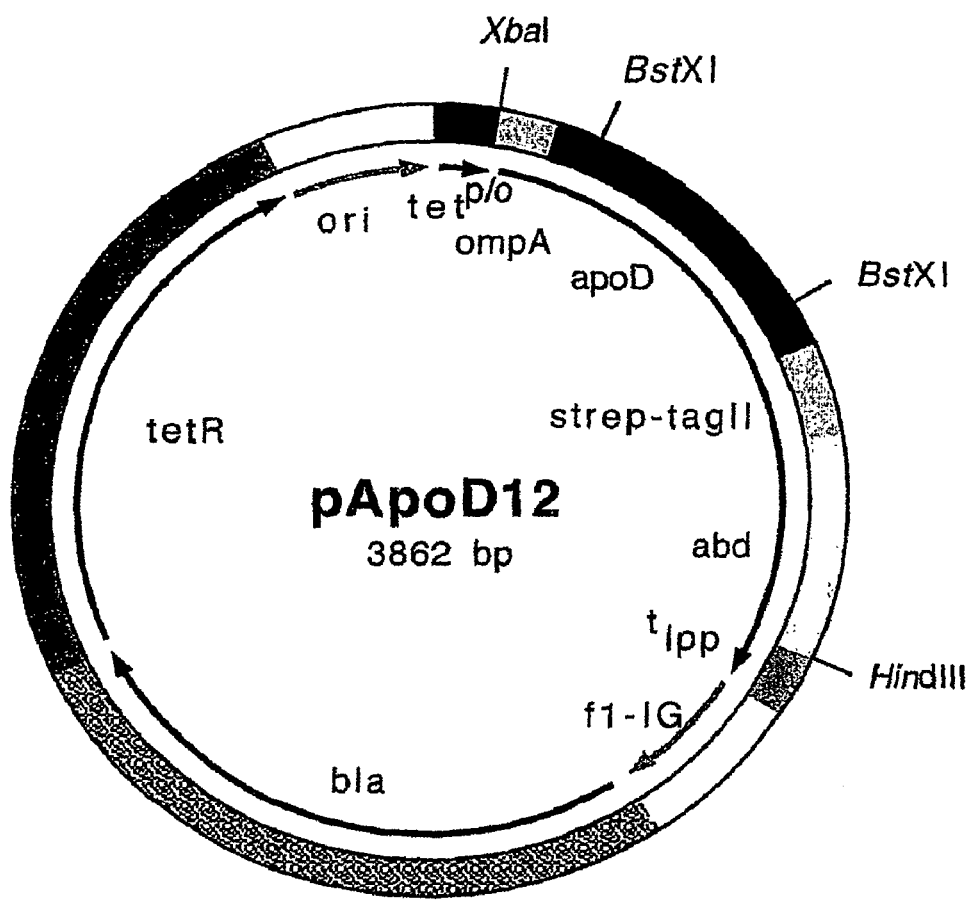
Figure 4:
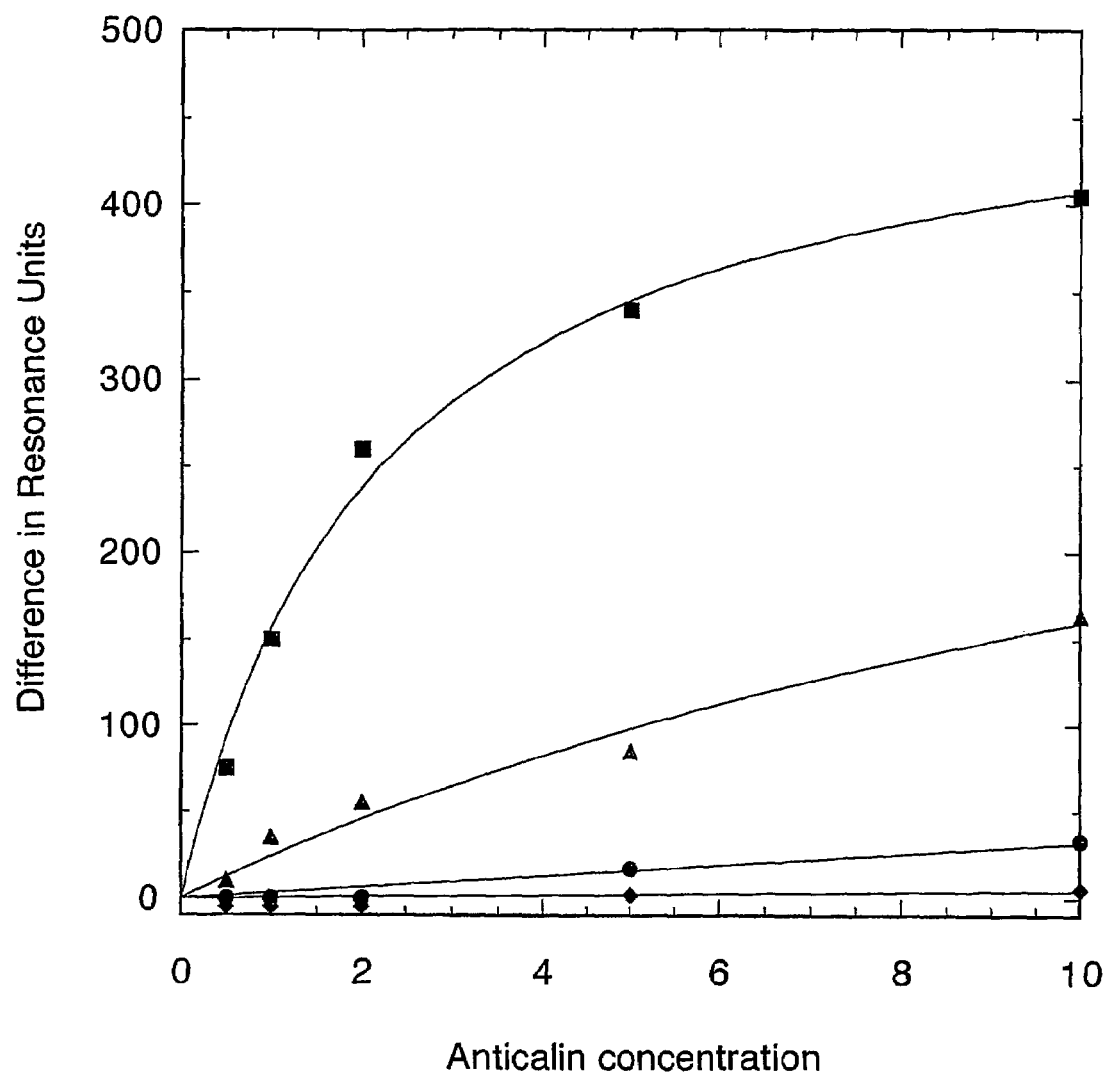

The invention is further illustrated by the following examples and the attached drawings in which:

FIG. 1 schematically illustrates the production of the library of lipocalin muteins at the nucleic acid level;

FIG. 2 schematically depicts the phasmid vector pApoD19;

FIG. 3 schematically depicts the expression vectors pApoD10 (A) and pApoD12 (B);

FIG. 4 depicts the binding of the anticalin HbgA to hemoglobin and corresponding control experiments with myoglobin and BSA, as well as a control experiments with ApoD and hemoglobin, measured via surface plasmon resonance.

FIG. 1 schematically shows a strategy for the concerted mutagenesis of 24 selected amino acid positions in the ApoD by repeated application of the polymerase chain reaction (PCR). Oligodeoxynucleotides were synthesized (SEQ ID NO:1, SEQ ID NO:2, SEQ ID NO:3 and SEQ ID NO:4) for each of the four peptide loops of this lipocalin in which the amino acids were to be mutated, wherein the respective mixtures of the building blocks given in the sequence protocol were employed at the mutation sites. Due to the composition chosen, from the altogether three possible stop codons only the amber stop codon TAG could possibly arise at the mutated codons, which is translated as glutamine in the E. coli supE-strains XL1-blue or TG1 used for gene expression. For certain applications, for example for gene expression in other bacterial strains or organisms, such a nonsense codon, if it arises in the structural gene for a selected mutein, can be substituted by a glutamine-encoding codon by the person skilled in the art, for example via site-directed mutagenesis. A nucleic acid fragment with 149 base pairs was amplified (Step 1, A) with the primers SEQ ID NO:1 and SEQ ID NO:2 using the pApoD10 plasmid-DNA (SEQ ID NO:11) containing the ApoD-structural gene as template. Parallel to this, a nucleic acid fragment with 148 base pairs was amplified (Step 1, B) with the primers SEQ ID NO:3 and SEQ ID NO:4, also using pApoD10 as template. The mixture of both of these fragments served as template in a second amplification step in the presence of an oligodeoxynucleotide SEQ ID NO:5 hybridizing with both of these fragments as well as the two flanking PCR primers SEQ ID NO:6 and SEQ ID NO:7, wherein a gene fragment of 369 base pairs was obtained. This fragment contained all 24 mutated codons and was subsequently cloned on the vector pApoD19 using both of the two BstXI-restriction sites. The use of these two restriction sites, the special arrangement of which led to two non-compatible overhanging DNA ends during the restriction digest, enabled an efficient ligation with unique orientation of the insert. The amino acid substitutions Leu23 to Pro, Pro133 to Val and Asn134 to Ala with respect to the original sequence of ApoD as well as a silent mutation in the codon Ala130 were previously accomplished in order to introduce both of the BstXI restriction sites at appropriate positions into the ApoD structural gene.

FIG. 2 shows a drawing of pApoD19 (SEQ ID NO: 10). This vector codes for a fusion protein from the OmpA signal sequence, a modified ApoD with the four amino acid substitutions Leu23 to Pro, Pro133 to Val, and Asn134 to Ala as well as Cys116 to Ser, a short linker (AlaGlyGlyAla), an amber stop codon, which is partially translated into Gln in an amber suppressor strain, and the coat protein pIII from M13, comprising its amino acids 3 to 406 (pIII). The structural gene is subject to the transcriptional control of the tetracycline promoter/operator (tet$^{p/o}$) and ends at the lipoprotein transcription terminator (t$_{lpp}$). Further elements of the vector are the origin of replication (ori), the intergenic region of the filamentous bacteriophage f1 (f1-IG), the chloramphenicol resistance gene (cat) coding for chloramphenicol-acetyl-transferase and the tetracycline repressor gene (tetR). An amber stop codon, which is partially read through in an amber suppressor host strain, is located between the coding region for ApoD with the OmpA signal sequence at its N-terminus followed by the linker at its C-terminus, and the coding region for the phage coat protein pIII. The BstXI restriction sites used for the cloning of the mutated gene cassette are labelled. A relevant segment from the nucleic acid sequence, beginning at the XbaI and ending with the HindIII restriction sites is depicted together with the encoded amino acid sequence (positions 144 to 1981 of SEQ ID NO:10) in the sequence listing as SEQ ID NO: 11.

FIG. 3 1shows a drawing of pApoD10 (A) and of pApoD12 (B). pApoD10 codes for a fusion protein made of the OmpA signal sequence, a modified ApoD according to FIG. 2 and the Strep-Tag® II as an affinity module. This structural gene is subject to the transcriptional control of the tetracycline-promoter/operator (tet$^{p/o}$) and ends at the lipoprotein transcription terminator (t$_{lpp}$). All further genetic elements are identical with pApoD19 according to FIG. 2. A relevant segment ranging from the XbaI restriction site to the HindIII restriction site from the nucleic acid sequence of pApoD10 is depicted together with the encoded amino acid sequence in the sequence listing as SEQ ID NO:11. Outside XbaI and HindIII restriction sites the vector is identical with the corresponding part of pApoD19 described in FIG. 2 (SEQ ID NO:10).

pApoD12 codes for a fusion protein made of the OmpA signal sequence, a modified ApoD according to FIG. 2, the Strep-Tag® II, and an albumin-binding domain (abd) of protein G from Streptococcus (Kraulis et al., FEBS Lett. 378 (1996), 190–194). Furthermore, it contains the structural gene for the ampicillin-resistance (bla) encoding the beta-lactamase instead of the cat gene for the chloramphenicol-resistance. All further genetic elements are identical with pASK75. A relevant segment from the nucleic acid sequence of pApoD12 (ranging from the XbaI restriction site to the HindIII restriction site) is given together with the encoded amino acid sequence in the sequence listing as SEQ ID NO:12. The vector elements outside this region are identical with the vector pASK75, the complete nucleotide sequence of which is given in the German patent publication DE 44 17 598 A1.

FIG. 4 shows a graphical representation of the data from Example 5, in which binding measurements with the anticalin HbgA were performed using surface plasmon resonance. Binding of HbgA to hemoglobin (squares) was compared with the interaction of ApoD and hemoglobin (circles). Furthermore, the anticalin HbgA does not bind to bovine serum albumin (rhombs) and binds just weakly to myoglobin (triangles), thus revealing pronounced specificity.

EXAMPLES

Example 1

Production of a Library for Muteins of ApoD

Unless otherwise indicated, genetic engineering methods known to the person skilled in the art were used, as for example described in Sambrook et al. (Molecular Cloning. A Laboratory Manual (1989), Cold Spring Harbor Press).

PCR was applied in multiple steps according to FIG. 1 for the concerted mutagenesis of in total 24 selected amino acid positions in the four peptide loops of ApoD. The PCR reactions were carried out in a volume of 50 μl in both of the first amplification steps, wherein 10 ng pApoD10 plasmid DNA were employed as template together with 25 pmol of the respective primers, which had been synthesized according to the conventional phosphoramidite method. In addition, the reaction mixture contained 5 μl 10×Taq buffer (100 mM Tris/HCl pH 9.0, 500 mM KCl, 1% v/v Triton X-100, 15 mM MgCl$_2$) and 4 μl dNTP-Mix (2.5 mM DATP, dCTP, dGTP, dTTP). After bringing to volume with water, the mixture was overlayed with mineral oil and was heated to 94° C. for 2 minutes in an automated thermocycler. Subsequently, 2.5 u Taq DNA-polymerase (5 u/μl, Promega) were added and 20 temperature cycles of 1 minute at 94° C., 1 minute at 60° C., and 1.5 minutes at 72° C. were carried out, followed by an incubation for 5 minutes at 60° C. The desired amplification products were isolated from Low Melting Point Agarose (Gibco BRL) by preparative agarose gel electrophoresis using the Jetsorb DNA extraction kit (Genomed) according to the instructions of the manufacturer.

For gene assembly the next amplification step was carried out in a 100 μl volume, wherein approximately 6 ng of both of these respective fragments were used as templates in the presence of 50 pmol of each of the primers SEQ ID NO:6 and SEQ ID NO:7 as well as 1 pmol of the oligodeoxynucleotide SEQ ID NO:5. The remaining components of the PCR mixture were added in the double amounts as in the previous amplification steps. PCR was carried out with 20 temperature cycles of 1 minute at 94° C., 1 minute at 60° C., 1.5 minutes at 72° C., followed by a subsequent incubation for 5 minutes at 60° C. The expected fragment was again isolated by preparative agarose gel electrophoresis.

For the cloning of this fragment, which represented the library of the ApoD muteins in nucleic acid form, it was first cut with the restriction enzyme BstXI (Hybaid) according to the instructions of the manufacturer. The resulting nucleic acid fragment (322 base pairs, bp) was purified by preparative agarose gel electrophoresis as above. The DNA of the vector pApoD19 was analogously cut with BstXI and the larger of the two fragments (4394 bp) was again isolated by preparative gel electrophoresis.

For the ligation, 3.2 μg (15 pmol) of the PCR fragment and 43 μg (15 pmol) of the vector fragment were incubated in the presence of 370 Weiss Units T4 DNA ligase (New England Biolabs) in a total volume of 1850 μl (50 mM Tris/HCl pH 7.8, 10 mM $MgCl_2$, 10 mM DTT, 1 mM ATP, 50 μg/ml BSA) for two days at 16° C. The DNA was subsequently precipitated by adding 50 μg tRNA from yeast (Boehringer Mannheim), 125 μl 5 M ammonium acetate, and 500 μl ethanol per each 120 μl of the ligation mixture. Incubation at −20° C. for three days was followed by centrifugation (30 minutes, 18500 g, 4° C.). Each precipitate was washed with 100 μl ethanol (70% v/v, −20° C.) and dried under vacuum. The DNA was finally dissolved and combined in 150 μl water.

The preparation of electrocompetent cells of the *E. coli* K12 strain XL1-blue (Bullock et al., supra) was performed according to the methods described by Tung and Chow (Trends Genet. 11 (1995), 128–129) and by Hengen (Trends Biochem. Sci. 21 (1996), 75–76). 1 l LB-medium containing 10 μg/ml tetracycline was adjusted by addition of a stationary XL1-blue overnight culture to an optical density at 600 nm of $OD_{600}$=0.08 and was incubated at 200 rpm and 26° C. in a 2 l Erlenmeyer flask. After reaching an $OD_{600}$=0.6, the culture was cooled for 30 minutes on ice and subsequently centrifuged for 15 minutes at 4000 g and 4° C. The cell sediment was washed twice each with 500 ml ice-cold 10% w/v glycerol and was finally resuspended in 2 ml of ice-cold GYT-medium (10% w/v glycerol, 0.125% w/v yeast extract, 0.25% w/v tryptone).

The MicroPulser system (Bio-Rad) was used with the accompanying cuvettes (electrode separation 2 mm) for the electroporation. All steps were carried out in the cold room at 4° C. 3.25 μl of the DNA solution from above (corresponding to 1 μg ligated DNA) was mixed with 100 μl of the cell suspension, was incubated 1 minute on ice, and was finally transferred to the cuvette. After the electroporation the suspension was immediately diluted in 2 ml of fresh, ice-cold SOC-medium (2% w/v tryptone, 0.5% w/v yeast extract, 10 mM NaCl, 10 mM $MgSO_4$, 10 mM $MgCl_2$) and was shaken for 60 minutes at 37° C. and 200 rpm. The culture was diluted in 1.5 l 2×YT-medium with 30 μg/ml chloramphenicol (LB/Cam) and cultivated until the $OD_{550}$ increased from a starting value of ca. 0.5 by 0.5 units. By employing in total 46 μg of the ligated DNA, $1.62\times10^9$ transformants were obtained in this way with altogether 46 electroporation runs. The transformants were further used according to Example 2.

Example 2

Phagemid Presentation and Selection of Anticalins Against Hemoglobin 200 ml of the culture (ca. 1.6 l) containing the cells from Example 1, which were transformed with the phasmid vectors coding for the library of the lipocalin muteins as fusion proteins, were transferred to a sterile Erlenmeyer flask. After infection with VCS-M13 helper phage (Strategene) at a multiplicity of infection of approximately 10 the cultur was shaken for additional 30 minutes at 37° C., 160 rpm. Kanamycin (70 μg/ml) was subsequently added, the incubator temperature was lowered to 26° C. and, after 10 minutes, anhydrotetracycline was added to 25 μg/l (25 μl of a 200 μg/ml stock solution in dimethylformamide, DMF) to induce gene expression. Incubation continued for another 7 hours at 26° C., 160 rpm.

From this culture, 50 ml were taken and the cells were sedimented by centrifugation (15 minutes, 12000 g, 4° C.). The supernatant containing the phagemid particles was sterile-filtered (0.45 μm), was mixed with ¼ volume (12.5 ml) 20% w/v PEG 8000, 15% w/v NaCl, and was incubated overnight at 4° C. After centrifugation (20 minutes, 18000 g, 4° C.) the precipitated phagemid particles were dissolved in 2 ml of cold PBS (4 mM $KH_2PO_4$, 16 mM $Na_2HPO_4$, 115 mM NaCl, pH 7.4). The solution was incubated on ice for 30 minutes and was distributed into two 1.5 ml reaction vessels. After centrifugation of undissolved components (5 minutes, 18500 g, 4° C.) each supernatant was transferred to a new reaction vessel.

Mixture with ¼ volume 20% w/v PEG 8000, 15% w/v NaCl and incubation for 30 to 60 minutes on ice was carried out in order to reprecipitate the phagemid particles. After centrifugation (20 minutes, 18500 g, 4° C.) the supernatant was removed and the precipitated phagemid particles were dissolved in a total of 1 ml PBS. After incubation for 30 minutes on ice the solution was cleared by centrifugation (5 minutes, 18500 g, 4° C.) and the supernatant was used directly for the affinity enrichment.

Immuno-sticks (NUNC) were used for the affinity enrichment of the recombinant phagemids carrying the anticalin fusion proteins. These were coated overnight with 800 μl of a solution of 500 μg/ml hemoglobin (Sigma) in PBS. Unoccupied binding sites on the surface of the Immuno-Stick were saturated by incubation with 1.2 ml 2% w/v BSA in PBST (PBS with 0.1% v/v Tween 20) for 2 hours at RT. Then, the Immuno-Stick was incubated in a mixture of 250 μl of the phagemid solution and 500 μl of blocking buffer (3% w/v BSA in PBST) for 1 hour at RT.

For the removal of non-bound phagemids, washing was performed eight times, each time with 950 μl PBST for 2 minutes. Adsorbed phagemids were finally eluted by 15 minutes treatment of the Immuno-Stick with 950 μl 0.1 M glycine/HCl pH 2.2, wherein the pH of the elution fraction was neutralized by mixing with 150 µl 0.5 M Tris immediately thereafter.

For the amplification, this phagemid solution (1.1 ml, containing between $10^6$ and $10^8$ colony-forming units depending on the selection cycle) was shortly warmed to 37° C., was mixed with 4 ml of an exponentially growing culture of E. coli XL1-blue ($OD_{550}$=0.5), and was incubated for 30 minutes at 37° C., 200 rpm. The cells infected with the phagemids were subsequently sedimented (2 minutes, 4420 g, 4° C.), were resuspended in 800 µl of fresh culture medium, and were plated out onto four agar plates with LB/Cam-medium (140 mm diameter).

After incubation for 14 hours at 32° C., the cells were scraped from the agar plates with respective addition of 10 ml 2×YT/Cam-medium, were transferred to a sterile Erlenmeyer-flask and were shaken for 20 minutes at 37° C., 200 rpm for complete suspension. 200 ml of 2×YT/Cam-medium prewarmed to 37° C. were inoculated to an $OD_{550}$=0.08 with an appropriate volume of this suspension.

For the repeated production and affinity enrichment of phagemid particles the same procedure as described at the beginning of this example was used.

Example 3

Identification of Hemoglobin-Binding Anticalins by Use of Colony Screening

For the analytical production of the anticalins as fusion proteins with the Strep-Tag II as well as with the albumin-binding domain and their characterization by "colony screening", the gene cassette between both BstXI cleavage sites was subcloned from the vector pApoD19 on pApoD12.

For this purpose the phasmid DNA was isolated from the mixture of the E. coli clones obtained by infection with the phagemids eluted during the last selection cycle from Example 2, using the QIAprep Spin Miniprep Kit (QIAGEN). The DNA was cut with the restriction enzyme BstXI and the smaller of the two fragments (322 bp) was purified by preparative agarose-gel electrophoresis as described in Example 1. The DNA of the vector pApoD12 was cut with BstXI and the larger of the two fragments (4394 bp) was isolated in the same way.

For the ligation, each 50 fmol of the two DNA-fragments were mixed with 1.5 Weiss Units T4 DNA ligase (Promega) in a total volume of 20 µl (30 mM Tris/HCl pH 7.8, 10 mM $MgCl_2$, 10 mM DTT, 1 mM ATP) and this was incubated overnight at 16° C. E. coli TG1-F⁻ (E. coli K12 TG1, which had lost its episome through repeated culturing under non-selective conditions) was transformed with 5 µl of this ligation mixture according to the $CaCl_2$-method (Sambrook et al., supra).

A hydrophilic PVDF membrane (Millipore, type GVWP, pore size 0.22 µm), labelled at one position and cut to size, was laid onto an LB/Amp agar plate and 150 µl of the cell suspension from the transformation batch were uniformly plated out onto this membrane. The plate was incubated for 6.5 hours at 37° C. in the incubation cabinet until the colonies had reached a diameter of ca. 0.5 mm.

In the meantime a hydrophobic membrane (Millipore, Immobilon P, pore size 0.45 µm), also cut to size, was moistened with PBS according to the instructions of the manufacturer. It was subsequently agitated for 4 hours at RT in a solution of 10 mg/ml human serum albumin (HSA, Sigma) in PBS. Remaining binding sites on the membrane were saturated by incubation with 3% w/v BSA, 0.5% v/v Tween 20 in PBS for 2 hours at RT. The membrane was washed twice for 10 minutes each with 20 ml PBS and agitated afterwards for 10 minutes in 10 ml LB/Amp medium, to which 200 µg/l anhydrotetracycline had been added. It was subsequently labelled at one position and was laid onto a culture plate with LB/Amp agar, which additionally contained 200 µg/l anhydrotetracycline. The hydrophilic membrane on which the colonies were grown was laid onto the hydrophobic membrane in such a way that both of the marks superimposed. The culture plate was incubated with both membranes at 22° C. for 15 hours. During this phase the respective ApoD muteins were secreted from the colonies and were immobilized via the albumin-binding domain on the HSA on the lower membrane.

After this, the upper membrane with the colonies was transferred to a fresh LB/Amp agar plate and stored at 4° C. The hydrophilic membrane was removed, was washed three times for 5 minutes each with 20 ml PBST, and was subsequently incubated 1 hour in 10 ml of a 1 µM solution of a conjugate of hemoglobin with digoxigenin in PBST.

For the production of the conjugate, a solution of 0.32 mg digoxigenin-3-O-methylcarbonyl-ε-aminocaproic acid-N-hydroxysuccinimide ester (Roche) in 25 µl DMSO was slowly added to 3.25 mg hemoglobin, which had been dissolved in 5 ml 5% w/v $NaHCO_3$ pH 8.0. After stirring for 1 hour at room temperature, the buffer containing excess reactant was removed to PBST by means of a PD-10 gel filtration column (Pharmacia) using PBST as running buffer.

After incubation with the conjugate, the membrane was washed three times with PBST, followed by incubation with 10 ml anti-digoxigenin-alkaline-phosphatase Fab fragment conjugate (Roche, dilution 1:1000 in PBST) for 1 hour. The membrane was subsequently washed for 5 minutes each twice with PBST and with PBS and agitated for 10 minutes in AP-buffer (0.1 M Tris/HCl pH 8.8, 0.1 M NaCl, 5 mM $MgCl_2$). For the chromogenic reaction, the membrane was incubated in 10 ml AP-buffer, to which 30 µl 5-Bromo-4-chloro-3-indolyl phosphat, p-Toluidin salt (Carl Roth) (50 µg/ml in dimethylformamide) and 5 µl Nitro Blue Tetrazolium (Sigma) (75 µg/ml in 70% v/v dimethylformamide) were added, until distinct colour signals could be recognized at the positions of some of the colonies. In this way binding activity for the protein ligand of the anticalins produced by these colonies was detected.

Eight of these colonies were cultured. The plasmid DNA was isolated and the mutated ApoD gene cassette was subjected to sequence analysis by use of the Genetic Analyzer 310 system with the ABI Prism BigDye Terminator Cycle Sequencing Ready Reaction Kit (both from Applied Biosystems) according to the instructions of the manufacturer. Herein the oligodesoxynucleotide SEQ ID NO:8 or the oligodesoxynucleotide SEQ ID NO:9 were used as sequencing primers. The eight sequenced clones exhibited only seven different sequences, which were named HbgA, HbgB, HbgC, HbgD, HbgE, HbgF, HbgG. The clone HbgA was found twice. The nucleotide sequences of the clones were translated into amino acid sequences and those amino acids deviating from ApoD are given in Table 1. The nucleotide sequences encoding the mutein HbgA and the amino acid sequence of the mutein HbgA are also shown in SEQ ID NO: 21.

TABLE 1

Sequence characteristics of selected ApoD muteins

| Amino Acid Position | ApoD | HbgA | HbgB | HbgC | HbgD | HbgE | HbgF | HbgG |
|---|---|---|---|---|---|---|---|---|
| 34 | Thr | Gln[a] | Phe | Ile | Tyr | Arg | Thr | Ala |
| 35 | Thr | Phe | Gln[a] | Gln[a] | Ala | Gln[a] | Met | Leu |
| 36 | Phe | Val | Val | Phe | Phe | Ile | Phe | Phe |
| 37 | Glu | Trp | Ser | Leu | Phe | Ser | Gln[a] | Trp |
| 38 | Asn | Met | Leu | Tyr | Val | Phe | Val | Phe |
| 60 | Glu | Phe | Val | His | Ala | Asp | Glu | Arg |
| 62 | Arg | Arg | Leu | His | Trp | Leu | Tyr | Ser |
| 63 | Ala | Ile | Tyr | Phe | Ala | Asn | Trp | Leu |
| 64 | Asp | Thr | Asn | Phe | Thr | Met | Tyr | Tyr |
| 65 | Gly | Leu | Val | Trp | Ser | Val | Asn | Gln |
| 66 | Thr | Asp | Tyr | Asn | Trp | Phe | Met | Ile |
| 68 | Asn | Trp | Thr | Leu | Val | Ala | Ile | Val |
| 89 | Phe | Glu | Leu | Val | Arg | Phe | Ser | Val |
| 90 | Ser | Gly | Thr | Gln | Ser | Ser | Val | Arg |
| 91 | Trp | Leu | Pro | Met | Arg | Gly | Leu | Pro |
| 92 | Phe | Gly | Leu | Val | Met | Phe | Tyr | Met |
| 93 | Met | Asp | Leu | Ser | Arg | Met | Val | Val |
| 115 | Thr | Glu | Met | Ala | Ser | Tyr | Ser | Gln[a] |
| 117 | Ile | Phe | Tyr | Phe | Ile | Ile | Tyr | Ser |
| 118 | Ile | Leu | Ile | Gln | Leu | Val | His | Ser |
| 119 | Gln | Trp | Thr | Leu | Trp | Ala | Leu | Ala |
| 120 | Leu | Leu | Val | Ser | Ile | Gln | Glu | Thr |
| 121 | Phe | Phe | Leu | Met | Asp | Tyr | Phe | Arg |
| 123 | Val | Trp | Ser[b] | Leu | Pro | Thr | Glu | Phe |
| 103 | Thr | | | | | | | Ile[c] |

[a]These glutamine acid residues were encoded by amber stop codons.
[b]At this position a cysteine residue introduced was found and replaced by serin.
[c]This amino acid substitution arose due to a random mutation outside the codons that were addressed by the mutagenesis PCR primers.

Example 4

Production of the Anticalins

For the preparative production of the anticalins the gene cassette between both BstXI-cleavage sites was subcloned from the pApoD12 vector on the expression plasmid pApoD10. The ApoD that was originally encoded on pApoD10 was furthermore produced as a control.

The DNA sequencing described in Example 3 had revealed the presence of an amber stop codon in all selected anticalins except HbgD (see Table 1). Moreover the clone HbgB carried an additional Cys residue. For efficient production of the anticalins the amber stop codons and the Cys codon were replaced with a Gln codon or a Ser codon, respectively. Therefore, the plasmids of the type pApoD10 carrying the genetic information for the muteins of ApoD were subjected to site-directed mutagenesis according to the methods described by Geisselsoder et al. (BioTechniques 5 (1987),786–791) and Kunkel et al. (Methods Enzymol. 154 (1987), 367–383) using the following oligodesoxynucleotides as mutagenic primers: HbgA, SEQ ID NO:13; HbgB, SEQ ID NO:14 and SEQ ID NO:15; HbgC, SEQ ID NO:16; HbgE: SEQ ID NO:17; HbgF, SEQ ID NO:18; HbgE SEQ ID NO:19. In each case the successful mutagenesis was confirmed by sequencing as described (see Example 3). Cells of E. coli JM83 (Yanisch-Perron et al., Gene 33 (1985), 103–119) were transformed according to the CaCl$_2$-method with the mutagenized plasmid and used for protein production.

The protein production was carried out at a 2 l scale. To this end, 50 ml of LB/Cam-medium were inoculated with a single colony of the JM83 transformant carrying the respective plasmid and was incubated overnight at 30° C., 200 rpm. 2 l of LB/Cam-medium in a 5 l-Erlenmeyer flask were then inoculated with the total volume of this preculture and were shaken at 22° C., 200 rpm to an OD$_{550}$=0.5. Induction was performed by adding 200 µg/l anhydrotetracycline (200 µl of a 2 mg/ml stock solution in DMF) and followed by shaking for 3 further hours at 22° C., 200 rpm.

The cells were sedimented by centrifugation (15 minutes, 4400 g, 4° C.) and, after decanting the supernatant, were resuspended in 20 ml ice-cold periplasmic release buffer (100 mM Tris/HCl pH 8.0, 500 mM sucrose, 1 mM EDTA). After incubation for 30 minutes on ice, the spheroplasts were sedimented by two subsequent centrifugation steps (15 minutes, 4400 g, 4° C. and 15 minutes, 30000 g, 4° C.). The supernatant was recovered as the periplasmatic protein extract and was dialyzed overnight against CP-buffer (100 mM Tris/HCl pH 8.0, 150 mM NaCl, 1 mM EDTA), was sterile-filtered, and was used for the following one-step purification.

The purification was carried out by means of the Strep-Tag II (Schmidt et al., supra) fused to the C-terminus of the ApoD mutein. In the present case the streptavidin mutein "1" was employed (German Patent Application 196 41 876.3; Voss and Skerra, Protein Eng. 10 (1997), 975–982), which was coupled to an NHS-activated sepharose (Pharmacia) at 5 mg/ml, relative to the bed volume of the matrix.

A 2 ml bed volume chromatography column filled with this material was equilibrated with 10 ml CP-buffer at 4° C. using a flow rate of 20 ml/h. Chromatography was monitored by measuring the absorption at 280 nm of the eluate in a flow-through photometer. After the application of the periplasmatic protein extract, the column was washed with CP-buffer until the base line was reached and the bound ApoD mutein was subsequently eluted with 10 ml of a solution of 2.5 mM D-desthiobiotin (Sigma) in CP buffer. The fractions containing the purified ApoD muteins were checked via SDS-polyacrylamide gel electrophoresis (Fling und Gregerson, Anal. Biochem. 155 (1986), 83–88) and were pooled. The protein yields were approximately 100 µg per 2 l culture.

Example 5

Measurement of the Affinity of the Anticalin HbgA for Hemoglobin

The binding affinity of the anticalin HbgA to hemoglobin was determined by surface plasmon resonance (SPR) using the BIAcore X system (BIACORE). Hemoglobin (100 µg/ml, dissolved in 10 mM maleate, pH 6.0) was immobilized at an amount of ca. 5000 resonance units (RU) to the surface of one flow channel on a CM5 sensor chip (BIACORE) using the amine coupling kit (BIACORE) according to the manufacturer's instructions. Unreacted groups on the biosensor chip surface were blocked with 1 M ethanolamine hydrochloride-NaOH pH 8.5. For the binding studies, HBS buffer (150 mM NaCl, 10 mM HEPES pH 7.4, 3.4 mM EDTA) containing 0.005% v/v surfactant P20 (BIACORE) was used as running buffer at a flow rate of 10 µl/min. Purified mutein HbgA (see Example 3) was dialysed against HBS, concentrated using Ultrafree-4 centrifugation filters (Millipore), and sterile-filtered (0.45 µm). The concentration of HbgA and also of ApoD were determined by absorption at 280 nm using a calculated extinction coefficient of 54600 $M^{-1}$ $cm^{-1}$ and 34150 $M^{-1}$ $cm^{-1}$, respectively (Gill and von Hippel, Anal. Biochem. 182 (1989), 319–326). The solution was diluted with HBS to a series of concentrations ranging from 10 µM to 0.5 µM, and surfactant P20 was added to a final concentration of 0.005%. The binding of HbgA to hemoglobin, immobilized on the sensor chip, was measured by applying each 75 µl of these protein solutions. Steady state resonance values were detected for the channel with the immobilized hemoglobin for each concentration applied. For each measurement the resonance value that was due to buffer effects and simultaneously measured for the second channel of the sensor chip, was subtracted, and the resulting difference value was plotted against the applied concentration. The data were fitted by non-linear least squares regression with the help of the computer program Kaleidagraph (Synergy software) according the equation $[P \cdot L] = ([P]_t [L]_t)/(K_d + [P]_t)$ whereby $[P]_t$ is the total cocentration of immobilized hemoglobin in (resonance units), $[L]_t$ is the concentration of the applied mutein or ApoD, $[P \cdot L]$ is the concentration of the formed complex (in resonance units) and $K_d$ is the dissociation constant.

Two sets of control experiments were performed. First, the bacterially produced ApoD was applied instead of its mutein HbgA, and binding to hemoglobin was measured in the same manner. Second, the binding of HbgA to myoglobin (Sigma) and to bovine serum albumin (BSA, Sigma) was measured. For this purpose, ca. 5000 RU of myoglobin and BSA, respectively, were immobilized on a CM5 sensor chip as described above, except using 100 µg/ml solutions in 10 mM acetate pH 4.7. The binding of HbgA was then measured as before.

All the binding curves are depicted in FIG. 4. A value of 2.2 µM was determined as the dissociation constant for the complex of the mutein HbgA and hemoglobin, while ApoD did not show detectable binding to hemoglobin. The mutein HbgA did not show detectable binding affinity to BSA and just weak binding to myoglobin, thus reflecting the known structural relationship with hemoglobin.

Accordingly, these results show that the method according to the present invention allows the generation of muteins of ApoD that not only have a high binding affinity to a native protein but that also have binding specifity for such a ligand. This finding is particularly surprising because up to now ApoD has only been known to bind low molecular weight ligands in a non-covalent manner but not to bind another protein (Vogt and Skerra, supra).

---

The invention claimed is:

1. A method for generating a mutein of human apolipoprotein D having detectable affinity to a given non-natural ligand of apolipoprotein D, comprising:

subjecting apolipoprotein D to mutagenesis at positions 34 to 38, 60, 62 to 66, 68, 89 to 93, 115, 117 to 121, and 123 of SEQ ID NO.: 22, resulting in a plurality of muteins of apolipoprotein D; and selecting and/or isolating any resulting muteins having binding affinity for a given ligand from the plurality of muteins.

2. A method according to claim 1, wherein said selecting comprises:

providing as given ligand a compound which is selected from the group consisting of a chemical compound in free or conjugated form that exhibits features of an immunological hapten, a peptide, a protein or another macromolecule, contacting the plurality of muteins with said ligand in order to allow formation of complexes between said ligand and muteins having binding affinity for said ligand, and removing muteins having no or no substantial binding affinity.

3. A method according to claim 1, wherein the ligand is a protein.

4. A method according to claim 1, wherein the selecting is carried out under competitive conditions.

5. A method according to claim 1, wherein a nucleic acid coding for the plurality of muteins of apolipoprotein D, which nucleic acid results from mutagenesis, is operably fused at the 3' end with a gene coding for the coat protein pIII of a filamentous bacteriophage of the M13-family or for a fragment of this coat protein, in order to select at least one mutein for the binding of the given ligand.

* * * * *

SEQUENCE LISTING

<160> NUMBER OF SEQ ID NOS: 25

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 1
gatggtacga aattgagaag atcccannkn nknnknnknn kggacgctgc atccagg        57

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 2
ggcttcacct tcgatttgmn ncacmnnmnn mnnmnnmnnc aamnnctggt ttaacacttt        60
gatc        64

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 3
gagcctgcca agctcgaggt taagnnknnk nnknnknnkc catcggcacc gtactg        56

<210> SEQ ID NO 4
<211> LENGTH: 64

```
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 4
ccaagatcca agcaaaatcm nngtgmnnmn nmnnmnnmnn actmnnacag gaatacacga      60
gggc                                                                  64

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 5
aacctcgagc ttggcaggct cagtgaggtt aactggggtg gcttcacctt cgatttg        57

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 6
gtgaataagt atccaggaag atggtacgaa attgagaag                            39

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 7
ctggagggag agccacgttt ctggccaaga tccaagcaaa atc                       43

<210> SEQ ID NO 8
<211> LENGTH: 27
<212> TYPE: DNA
```

-continued

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
cccaagcatt tcatcttggg aagtgcc                                    27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
gctgagcttg gggcagttca cctgg                                      25

<210> SEQ ID NO 10
<211> LENGTH: 4716
<212> TYPE: DNA
<213> ORGANISM: Artificial Sequence
<220> FEATURE:
<223> OTHER INFORMATION: Description of Artificial Sequence: Synthetic
      nucleotide sequence construct

<400> SEQUENCE: 10
ccataacgct cggttgccgc cgggcgtttt ttattggcca gatgattaat tcctaatttt    60
tgttgacact ctatcattga tagagttatt ttaccactcc ctatcagtga tagagaaaag   120
tgaaatgaat agttcgacaa aaatctagat aacgagggca aaaatgaaa aagacagcta   180 tcgcgattgc agtggctctg gctggcttcg ctaccgtagc gcaggcccaa gcatttcatc   240
ttgggaagtg ccccaatcct ccggtgcagg agaattttga cgtgaataag tatccaggaa   300
gatggtacga aattgagaag atcccaacaa cctttgagaa tggacgctgc atccaggcca   360
actactcact aatggaaaac ggaaagatca agtgttaaaa ccaggagttg agagctgatg   420
gaactgtgaa tcaaatcgaa ggtgaagcca ccccagttaa cctcacagag cctgccaagc   480
tggaagttaa gttttcctgg tttatgccat cggcaccgta ctggatcctg gccaccgact   540
atgagaacta tgccctcgtg tattcctgta ctagtatcat ccaactttt cacgtggatt   600 ttgcttggat cttggccaga aacgtggctc tccctccaga aacagtggac tctctaaaaa   660
atatcctgac ttctaataac attgatgtca agaaaatgac ggtcacagac caggtgaact   720
gccccaagct cagcgctggt ggggcctaga ctgttgaaag ttgtttagca aaacccata   780 cagaaaattc atttactaac gtctggaaag acgacaaaac tttagatcgt tacgctaact   840
atgagggctg tctgtggaat gctacaggcg ttgtagtttg tactggtgac gaaactcagt   900
gttacggtac atgggttcct attgggcttg ctatccctga aaatgagggt ggtggctctg   960
agggtggcgg ttctgagggt ggcggttctg agggtggcgg tactaaacct cctgagtacg  1020
gtgatacacc tattccgggc tatacttata tcaaccctct cgacggcact tatccgcctg  1080
gtactgagca aaaccccgct aatcctaatc cttctcttga ggagtctcag cctcttaata  1140
ctttcatgtt tcagaataat aggttccgaa ataggcaggg gcattaact gtttatacgg  1200 gcactgttac tcaaggcact gaccccgtta aacttatta ccagtacact cctgtatcat  1260
caaaagccat gtatgacgct tactggaacg gtaaattcag agactgcgct ttccattctg  1320
gctttaatga ggatccattc gtttgtgaat atcaaggcca atcgtctgac ctgcctcaac  1380
ctcctgtcaa tgctggcggc ggctctggtg gtggttctgg tggcggctct gagggtggtg  1440

-continued

```
gctctgaggg tggcggttct gagggtggcg gctctgaggg aggcggttcc ggtggtggct      1500
ctggttccgg tgattttgat tatgaaagaa tggcaaacgc taataagggg gctatgaccg      1560
aaaatgccga tgaaaacgcg ctacagtctg acgctaaagg caaacttgat tctgtcgcta      1620
ctgattacgg tgctgctatc gatggtttca ttggtgacgt ttccggcctt gctaatggta      1680
atggtgctac tggtgatttt gctggctcta attcccaaat ggctcaagtc ggtgacggtg      1740
ataattcacc tttaatgaat aatttccgtc aatatttacc ttccctccct caatcggttg      1800
aatgtcgccc ttttgtcttt ggcgctggta accatatga attttctatt gattgtgaca      1860
aaataaactt attccgtggt gtctttgcgt ttcttttata tgttgccacc tttatgtatg      1920
tattttctac gtttgctaac atactgcgta ataaggagtc ttaataagct tgacctgtga      1980
agtgaaaaat ggcgcacatt gtgcgacatt ttttttgtct gccgtttacc gctactgcgt      2040
cacggatctc cacgcgccct gtagcggcgc attaagcgcg gcgggtgtgg tggttacgcg      2100
cagcgtgacc gctacacttg ccagcgccct agcgcccgct cctttcgctt tcttcccttc      2160
ctttctcgcc acgttcgccg gctttccccg tcaagctcta aatcggggc tccctttagg      2220 gttccgattt agtgctttac ggcacctcga ccccaaaaaa cttgattagg gtgatggttc      2280
acgtagtggg ccatcgccct gatagacggt ttttcgccct tgacgttgg agtccacgtt      2340 ctttaatagt ggactcttgt tccaaactgg aacaacactc aaccctatct cggtctattc      2400
ttttgattta agggcattt tgccgatttc ggcctattgg ttaaaaaatg agctgattta      2460
acaaaaattt aacgcgaatt ttaacaaaat tggcgaaaa tgagacgttg atcggcacgt      2520
aagaggttcc aactttcacc ataatgaaat aagatcacta ccgggcgtat ttttttgagtt      2580 atcgagattt tcaggagcta aggaagctaa atgggagaaa aaaatcactg gatataccac      2640
cgttgatata tcccaatggc atcgtaaaga acattttgag gcatttcagt cagttgctca      2700
atgtacctat aaccgaccg ttcagctgga tattacggcc ttttttaaga ccgtaaagaa      2760
aaataagcac aagttttatc cggcctttat tcacattctt gcccgcctga tgaatgctca      2820
tccggaattc cgtatggcaa tgaaagacgg tgagctggtg atatgggata gtgttcaccc      2880
ttgttacacc gttttccatg agcaaactga aacgttttca tcgctctgga gtgaatacca      2940
cgacgatttc cggcagtttc tacacatata ttcgcaagat gtggcgtgtt acggtgaaaa      3000
cctggcctat ttccctaaag ggtttattga gaatatgttt ttcgtctcag ccaatccctg      3060
ggtgagtttc accagttttg atttaaacgt ggccaatatg gacaacttct tcgcccccgt      3120
tttcactatg ggcaaatatt atacgcaagg cgacaaggtg ctgatgccgc tggcgattca      3180
ggttcatcat gccgtttgtg atggcttcca tgtcggcaga atgcttaatg aattacaaca      3240
gtactgcgat gagtggcagg cggggcgta ataggaatta atgatgtctc gtttagataa      3300
aagtaaagtg attaacagcg cattagagct gcttaatgag gtcggaatcg aaggtttaac      3360
aacccgtaaa ctcgcccaga agctaggtgt agagcagcct acattgtatt ggcatgtaaa      3420
aaataagcgg gctttgctcg acgccttagc cattgagatg ttagataggc accatactca      3480
cttttgccct ttagaagggg aaagctggca agatttttta cgtaataacg ctaaaagttt      3540
tagatgtgct ttactaagtc atcgcgatgg agcaaaagta catttaggta cacggcctac      3600
agaaaaacag tatgaaactc tcgaaaatca attagccttt ttatgccaac aaggttttc      3660 actagagaat gcattatatg cactcagcgc agtgggggcat tttactttag gttgcgtatt      3720
ggaagatcaa gagcatcaag tcgctaaaga agaaagggaa acacctacta ctgatagtat      3780
gccgccatta ttacgacaag ctatcgaatt atttgatcac caaggtgcag agccagcctt      3840
```

```
cttattcggc cttgaattga tcatatgcgg attagaaaaa caacttaaat gtgaaagtgg    3900
gtcttaaaag cagcataacc ttttccgtg atggtaactt cactagttta aaaggatcta     3960
ggtgaagatc cttttgata atctcatgac caaaatccct taacgtgagt tttcgttcca    4020
ctgagcgtca gacccgtag aaaagatcaa aggatcttct tgagatcctt ttttctgcg     4080 cgtaatctgc tgcttgcaaa caaaaaaacc accgctacca gcggtggttt gtttgccgga   4140
tcaagagcta ccaactcttt ttccgaaggt aactggcttc agcagagcgc agataccaaa   4200
tactgtcctt ctagtgtagc cgtagttagg ccaccacttc aagaactctg tagcaccgcc   4260 tacataccte gctctgctaa tcctgttacc agtggctgct gccagtggcg ataagtcgtg   4320
tcttaccggg ttggactcaa gacgatagtt accggataag gcgcagcggt cgggctgaac   4380
ggggggttcg tgcacacagc ccagcttgga gcgaacgacc tacaccgaac tgagatacct   4440
acagcgtgag ctatgagaaa gcgccacgct tcccgaaggg agaaaggcgg acaggtatcc   4500
ggtaagcggc agggtcggaa caggagagcg cacgagggag cttccagggg gaaacgcctg   4560
gtatctttat agtcctgtcg ggtttcgcca cctctgactt gagcgtcgat ttttgtgatg   4620
ctcgtcaggg gggcggagcc tatggaaaaa cgccagcaac gcggcctttt tacggttcct   4680
ggccttttgc tggccttttg ctcacatgac ccgaca                              4716
```

<210> SEQ ID NO 11
<211> LENGTH: 1828
<212> TYPE: DNA
<213> ORGANISM: Artificial Sequence
<220> FEATURE:
<223> OTHER INFORMATION: Description of Artificial Sequence: Synthetic
      nucleotide sequence construct
<220> FEATURE:
<221> NAME/KEY: sig_peptide
<222> LOCATION: (22)..(84)
<220> FEATURE:
<221> NAME/KEY: CDS
<222> LOCATION: (22)..(84)
<220> FEATURE:
<221> NAME/KEY: mat_peptide
<222> LOCATION: (85)..(1818)
<220> FEATURE:
<221> NAME/KEY: CDS
<222> LOCATION: (85)..(591)
<223> OTHER INFORMATION: mature ApoD
<220> FEATURE:
<221> NAME/KEY: CDS
<222> LOCATION: (592)..(603)
<223> OTHER INFORMATION: codes linker Ala-Gly-Gly-Ala
<220> FEATURE:
<221> NAME/KEY: CDS
<222> LOCATION: (604)..(606)
<223> OTHER INFORMATION: amber stop codon
<220> FEATURE:
<221> NAME/KEY: CDS
<222> LOCATION: (607)..(1818)
<223> OTHER INFORMATION: codes amino acids 3-406 of coat protein pIII

<400> SEQUENCE: 11

```
tctagataac gagggcaaaa a atg aaa aag aca gct atc gcg att gca gtg           51
                        Met Lys Lys Thr Ala Ile Ala Ile Ala Val
                            -20                      -15 gca ctg gct ggt ttc gct acc gta gcg cag gcc caa gca ttt cat ctt           99
Ala Leu Ala Gly Phe Ala Thr Val Ala Gln Ala Gln Ala Phe His Leu
    -10              -5              -1   1               5 ggg aag tgc ccc aat cct ccg gtg cag gag aat ttt gac gtg aat aag         147
Gly Lys Cys Pro Asn Pro Pro Val Gln Glu Asn Phe Asp Val Asn Lys
                10              15                  20
```

```
tat cca gga aga tgg tac gaa att gag aag atc cca aca acc ttt gag        195
Tyr Pro Gly Arg Trp Tyr Glu Ile Glu Lys Ile Pro Thr Thr Phe Glu
            25                  30                  35 aat gga cgc tgc atc cag gcc aac tac tca cta atg gaa aac gga aag        243
Asn Gly Arg Cys Ile Gln Ala Asn Tyr Ser Leu Met Glu Asn Gly Lys
        40                  45                  50 atc aaa gtg tta aac cag gag ttg aga gct gat gga act gtg aat caa        291
Ile Lys Val Leu Asn Gln Glu Leu Arg Ala Asp Gly Thr Val Asn Gln
55                  60                  65 atc gaa ggt gaa gcc acc cca gtt aac ctc aca gag cct gcc aag ctg        339
Ile Glu Gly Glu Ala Thr Pro Val Asn Leu Thr Glu Pro Ala Lys Leu
70                  75                  80                  85 gaa gtt aag ttt tcc tgg ttt atg cca tcg gca ccg tac tgg atc ctg        387
Glu Val Lys Phe Ser Trp Phe Met Pro Ser Ala Pro Tyr Trp Ile Leu
                90                  95                  100 gcc acc gac tat gag aac tat gcc ctc gtg tat tcc tgt act agt atc        435
Ala Thr Asp Tyr Glu Asn Tyr Ala Leu Val Tyr Ser Cys Thr Ser Ile
            105                 110                 115 atc caa ctt ttt cac gtg gat ttt gct tgg atc ttg gcc aga aac gtg        483
Ile Gln Leu Phe His Val Asp Phe Ala Trp Ile Leu Ala Arg Asn Val
        120                 125                 130 gct ctc cct cca gaa aca gtg gac tct cta aaa aat atc ctg act tct        531
Ala Leu Pro Pro Glu Thr Val Asp Ser Leu Lys Asn Ile Leu Thr Ser
135                 140                 145 aat aac att gat gtc aag aaa atg acg gtc aca gac cag gtg aac tgc        579
Asn Asn Ile Asp Val Lys Lys Met Thr Val Thr Asp Gln Val Asn Cys
150                 155                 160                 165 ccc aag ctc agc gct ggt ggg gcc tag act gtt gaa agt tgt tta gca        627
Pro Lys Leu Ser Ala Gly Gly Ala Gln Thr Val Glu Ser Cys Leu Ala
                170                 175                 180 aaa ccc cat aca gaa aat tca ttt act aac gtc tgg aaa gac gac aaa        675
Lys Pro His Thr Glu Asn Ser Phe Thr Asn Val Trp Lys Asp Asp Lys
            185                 190                 195 act tta gat cgt tac gct aac tat gag ggc tgt ctg tgg aat gct aca        723
Thr Leu Asp Arg Tyr Ala Asn Tyr Glu Gly Cys Leu Trp Asn Ala Thr
        200                 205                 210 ggc gtt gta gtt tgt act ggt gac gaa act cag tgt tac ggt aca tgg        771
Gly Val Val Val Cys Thr Gly Asp Glu Thr Gln Cys Tyr Gly Thr Trp
215                 220                 225 gtt cct att ggg ctt gct atc cct gaa aat gag ggt ggt ggc tct gag        819
Val Pro Ile Gly Leu Ala Ile Pro Glu Asn Glu Gly Gly Gly Ser Glu
230                 235                 240                 245 ggt ggc ggt tct gag ggt ggc ggt tct gag ggt ggc ggt act aaa cct        867
Gly Gly Gly Ser Glu Gly Gly Gly Ser Glu Gly Gly Gly Thr Lys Pro
                250                 255                 260 cct gag tac ggt gat aca cct att ccg ggc tat act tat atc aac cct        915
Pro Glu Tyr Gly Asp Thr Pro Ile Pro Gly Tyr Thr Tyr Ile Asn Pro
            265                 270                 275 ctc gac ggc act tat ccg cct ggt act gag caa aac ccc gct aat cct        963
Leu Asp Gly Thr Tyr Pro Pro Gly Thr Glu Gln Asn Pro Ala Asn Pro
        280                 285                 290 aat cct tct ctt gag gag tct cag cct ctt aat act ttc atg ttt cag       1011
Asn Pro Ser Leu Glu Glu Ser Gln Pro Leu Asn Thr Phe Met Phe Gln
295                 300                 305 aat aat agg ttc cga aat agg cag ggg gca tta act gtt tat acg ggc       1059
Asn Asn Arg Phe Arg Asn Arg Gln Gly Ala Leu Thr Val Tyr Thr Gly
310                 315                 320                 325 act gtt act caa ggc act gac ccc gtt aaa act tat tac cag tac act       1107
Thr Val Thr Gln Gly Thr Asp Pro Val Lys Thr Tyr Tyr Gln Tyr Thr
                330                 335                 340
```

```
cct gta tca tca aaa gcc atg tat gac gct tac tgg aac ggt aaa ttc      1155
Pro Val Ser Ser Lys Ala Met Tyr Asp Ala Tyr Trp Asn Gly Lys Phe
            345                 350                 355 aga gac tgc gct ttc cat tct ggc ttt aat gag gat cca ttc gtt tgt      1203
Arg Asp Cys Ala Phe His Ser Gly Phe Asn Glu Asp Pro Phe Val Cys
        360                 365                 370 gaa tat caa ggc caa tcg tct gac ctg cct caa cct cct gtc aat gct      1251
Glu Tyr Gln Gly Gln Ser Ser Asp Leu Pro Gln Pro Pro Val Asn Ala
375                 380                 385 ggc ggc ggc tct ggt ggt ggt tct ggt ggc ggc tct gag ggt ggt ggc      1299
Gly Gly Gly Ser Gly Gly Gly Ser Gly Gly Gly Ser Glu Gly Gly Gly
390                 395                 400                 405 tct gag ggt ggc ggt tct gag ggt ggc ggc tct gag gga ggc ggt tcc      1347
Ser Glu Gly Gly Gly Ser Glu Gly Gly Gly Ser Glu Gly Gly Gly Ser
            410                 415                 420 ggt ggc ggc tct ggt tcc ggt gat ttt gat tat gaa aag atg gca aac      1395
Gly Gly Gly Ser Gly Ser Gly Asp Phe Asp Tyr Glu Lys Met Ala Asn
        425                 430                 435 gct aat aag ggg gct atg acc gaa aat gcc gat gaa aac gcg cta cag      1443
Ala Asn Lys Gly Ala Met Thr Glu Asn Ala Asp Glu Asn Ala Leu Gln
440                 445                 450 tct gac gct aaa ggc aaa ctt gat tct gtc gct act gat tac ggt gct      1491
Ser Asp Ala Lys Gly Lys Leu Asp Ser Val Ala Thr Asp Tyr Gly Ala
455                 460                 465 gct atc gat ggt ttc att ggt gac gtt tcc ggc ctt gct aat ggt aat      1539
Ala Ile Asp Gly Phe Ile Gly Asp Val Ser Gly Leu Ala Asn Gly Asn
470                 475                 480                 485 ggt gct act ggt gat ttt gct ggc tct aat tcc caa atg gct caa gtc      1587
Gly Ala Thr Gly Asp Phe Ala Gly Ser Asn Ser Gln Met Ala Gln Val
            490                 495                 500 ggt gac ggt gat aat tca cct tta atg aat aat ttc cgt caa tat tta      1635
Gly Asp Gly Asp Asn Ser Pro Leu Met Asn Asn Phe Arg Gln Tyr Leu
        505                 510                 515 cct tcc ctc cct caa tcg gtt gaa tgt cgc cct ttt gtc ttt ggc gct      1683
Pro Ser Leu Pro Gln Ser Val Glu Cys Arg Pro Phe Val Phe Gly Ala
520                 525                 530 ggt aaa cca tat gaa ttt tct att gat tgt gac aaa ata aac tta ttc      1731
Gly Lys Pro Tyr Glu Phe Ser Ile Asp Cys Asp Lys Ile Asn Leu Phe
535                 540                 545 cgt ggt gtc ttt gcg ttt ctt tta tat gtt gcc acc ttt atg tat gta      1779
Arg Gly Val Phe Ala Phe Leu Leu Tyr Val Ala Thr Phe Met Tyr Val
550                 555                 560                 565 ttt tct acg ttt gct aac ata ctg cgt aat aag gag tct taataagctt      1828
Phe Ser Thr Phe Ala Asn Ile Leu Arg Asn Lys Glu Ser
            570                 575

<210> SEQ ID NO 12
<211> LENGTH: 628
<212> TYPE: DNA
<213> ORGANISM: Artificial Sequence
<220> FEATURE:
<223> OTHER INFORMATION: Description of Artificial Sequence: Synthetic
      nucleotide sequence construct
<220> FEATURE:
<221> NAME/KEY: sig_peptide
<222> LOCATION: (22)..(84)
<220> FEATURE:
<221> NAME/KEY: CDS
<222> LOCATION: (22)..(84)
<220> FEATURE:
<221> NAME/KEY: mat_peptide
<222> LOCATION: (85)..(618)
<220> FEATURE:
```

<221> NAME/KEY: CDS
<222> LOCATION: (85)..(591)
<223> OTHER INFORMATION: mature ApoD
<220> FEATURE:
<221> NAME/KEY: CDS
<222> LOCATION: (592)..(618)
<223> OTHER INFORMATION: Strep-tag II affinity tag

<400> SEQUENCE: 12

```
tctagataac gagggcaaaa a atg aaa aag aca gct atc gcg att gca gtg          51
                        Met Lys Lys Thr Ala Ile Ala Ile Ala Val
                             -20                 -15 gca ctg gct ggt ttc gct acc gta gcg cag gcc caa gca ttt cat ctt          99
Ala Leu Ala Gly Phe Ala Thr Val Ala Gln Ala Gln Ala Phe His Leu
-10             -5              -1   1               5 ggg aag tgc ccc aat cct ccg gtg cag gag aat ttt gac gtg aat aag         147
Gly Lys Cys Pro Asn Pro Pro Val Gln Glu Asn Phe Asp Val Asn Lys
            10              15                  20 tat cca gga aga tgg tac gaa att gag aag atc cca aca acc ttt gag         195
Tyr Pro Gly Arg Trp Tyr Glu Ile Glu Lys Ile Pro Thr Thr Phe Glu
        25                  30                  35 aat gga cgc tgc atc cag gcc aac tac tca cta atg gaa aac gga aag         243
Asn Gly Arg Cys Ile Gln Ala Asn Tyr Ser Leu Met Glu Asn Gly Lys
    40                  45                  50 atc aaa gtg tta aac cag gag ttg aga gct gat gga act gtg aat caa         291
Ile Lys Val Leu Asn Gln Glu Leu Arg Ala Asp Gly Thr Val Asn Gln
55                  60                  65 atc gaa ggt gaa gcc acc cca gtt aac ctc aca gag cct gcc aag ctg         339
Ile Glu Gly Glu Ala Thr Pro Val Asn Leu Thr Glu Pro Ala Lys Leu
70                  75                  80                  85 gaa gtt aag ttt tcc tgg ttt atg cca tcg gca ccg tac tgg atc ctg         387
Glu Val Lys Phe Ser Trp Phe Met Pro Ser Ala Pro Tyr Trp Ile Leu
                90                  95                  100 gcc acc gac tat gag aac tat gcc ctc gtg tat tcc tgt act agt atc         435
Ala Thr Asp Tyr Glu Asn Tyr Ala Leu Val Tyr Ser Cys Thr Ser Ile
                105                 110                 115 atc caa ctt ttt cac gtg gat ttt gct tgg atc ttg gcc aga aac gtg         483
Ile Gln Leu Phe His Val Asp Phe Ala Trp Ile Leu Ala Arg Asn Val
            120                 125                 130 gct ctc cct cca gaa aca gtg gac tct cta aaa aat atc ctg act tct         531
Ala Leu Pro Pro Glu Thr Val Asp Ser Leu Lys Asn Ile Leu Thr Ser
135                 140                 145 aat aac att gat gtc aag aaa atg acg gtc aca gac cag gtg aac tgc         579
Asn Asn Ile Asp Val Lys Lys Met Thr Val Thr Asp Gln Val Asn Cys
150                 155                 160                 165 ccc aag ctc agc gct tgg tct cac ccg cag ttc gaa aaa taataagctt          628
Pro Lys Leu Ser Ala Trp Ser His Pro Gln Phe Glu Lys
                170                 175
```

<210> SEQ ID NO 13
<211> LENGTH: 775
<212> TYPE: DNA
<213> ORGANISM: Artificial Sequence
<220> FEATURE:
<223> OTHER INFORMATION: Description of Artificial Sequence: Synthetic
      nucleotide sequence construct
<220> FEATURE:
<221> NAME/KEY: sig_peptide
<222> LOCATION: (22)..(84)
<220> FEATURE:
<221> NAME/KEY: CDS
<222> LOCATION: (22)..(84)
<220> FEATURE:
<221> NAME/KEY: mat_peptide
<222> LOCATION: (85)..(765)

<223> OTHER INFORMATION: fusion protein of modified ApoD, Strep-tag II
      and albumin binding domain
<220> FEATURE:
<221> NAME/KEY: CDS
<222> LOCATION: (85)..(591)
<223> OTHER INFORMATION: mature ApoD
<220> FEATURE:
<221> NAME/KEY: CDS
<222> LOCATION: (592)..(618)
<223> OTHER INFORMATION: Strep-tag II affinity tag
<220> FEATURE:
<221> NAME/KEY: CDS
<222> LOCATION: (619)..(765)
<223> OTHER INFORMATION: albumin binding domain of Protein G

<400> SEQUENCE: 13

```
tctagataac gagggcaaaa a atg aaa aag aca gct atc gcg att gca gtg            51
                        Met Lys Lys Thr Ala Ile Ala Ile Ala Val
                        -20                 -15 gca ctg gct ggt ttc gct acc gta gcg cag gcc caa gca ttt cat ctt           99
Ala Leu Ala Gly Phe Ala Thr Val Ala Gln Ala Gln Ala Phe His Leu
    -10             -5                  -1  1               5 ggg aag tgc ccc aat cct ccg gtg cag gag aat ttt gac gtg aat aag          147
Gly Lys Cys Pro Asn Pro Pro Val Gln Glu Asn Phe Asp Val Asn Lys
              10                  15                  20 tat cca gga aga tgg tac gaa att gag aag atc cca aca acc ttt gag          195
Tyr Pro Gly Arg Trp Tyr Glu Ile Glu Lys Ile Pro Thr Thr Phe Glu
          25                  30                  35 aat gga cgc tgc atc cag gcc aac tac tca cta atg gaa aac gga aag          243
Asn Gly Arg Cys Ile Gln Ala Asn Tyr Ser Leu Met Glu Asn Gly Lys
      40                  45                  50 atc aaa gtg tta aac cag gag ttg aga gct gat gga act gtg aat caa          291
Ile Lys Val Leu Asn Gln Glu Leu Arg Ala Asp Gly Thr Val Asn Gln
  55                  60                  65 atc gaa ggt gaa gcc acc cca gtt aac ctc aca gag cct gcc aag ctg          339
Ile Glu Gly Glu Ala Thr Pro Val Asn Leu Thr Glu Pro Ala Lys Leu
70                  75                  80                  85 gaa gtt aag ttt tcc tgg ttt atg cca tcg gca ccg tac tgg atc ctg          387
Glu Val Lys Phe Ser Trp Phe Met Pro Ser Ala Pro Tyr Trp Ile Leu
                90                  95                 100 gcc acc gac tat gag aac tat gcc ctc gtg tat tcc tgt act agt atc          435
Ala Thr Asp Tyr Glu Asn Tyr Ala Leu Val Tyr Ser Cys Thr Ser Ile
            105                 110                 115 atc caa ctt ttt cac gtg gat ttt gct tgg atc ttg gcc aga aac gtg          483
Ile Gln Leu Phe His Val Asp Phe Ala Trp Ile Leu Ala Arg Asn Val
        120                 125                 130 gct ctc cct cca gaa aca gtg gac tct cta aaa aat atc ctg act tct          531
Ala Leu Pro Pro Glu Thr Val Asp Ser Leu Lys Asn Ile Leu Thr Ser
    135                 140                 145 aat aac att gat gtc aag aaa atg acg gtc aca gac cag gtg aac tgc          579
Asn Asn Ile Asp Val Lys Lys Met Thr Val Thr Asp Gln Val Asn Cys
150                 155                 160                 165 ccc aag ctc agc gct tgg tct cac ccg cag ttc gaa aaa cca gct agc          627
Pro Lys Leu Ser Ala Trp Ser His Pro Gln Phe Glu Lys Pro Ala Ser
                170                 175                 180 ctg gct gaa gct aaa gtt ctg gct aac cgt gaa ctg gac aaa tac ggt          675
Leu Ala Glu Ala Lys Val Leu Ala Asn Arg Glu Leu Asp Lys Tyr Gly
            185                 190                 195 gtt tcc gac tac tac aaa aac ctc atc aac aac gct aaa acc gtt gaa          723
Val Ser Asp Tyr Tyr Lys Asn Leu Ile Asn Asn Ala Lys Thr Val Glu
        200                 205                 210 ggt gtt aaa gct ctg atc gac gaa att ctc gca gca ctg ccg                  765
Gly Val Lys Ala Leu Ile Asp Glu Ile Leu Ala Ala Leu Pro
    215                 220                 225
```

-continued

```
          215                 220                 225
taataagctt                                                          775

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 14
cccatccaaa caaactgtgg gatcttct                                       28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 15
gtcccaaaga aacctgaaat gggatctt                                       28

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 16
ttcaagcaaa atcagagtga agaaccg                                        27

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 17
gtccataaag aaactgaatt gggatctt                                       28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 18
gtccaaacga aatctgccgt gggatctt                                       28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 19
gcagcgtccc acctgaaaca tagttggg                                       28

<210> SEQ ID NO 20
<211> LENGTH: 26
```

```
<212> TYPE: DNA
<213> ORGANISM: Artificial Sequence
<220> FEATURE:
<223> OTHER INFORMATION: Description of Artificial Sequence: Primer

<400> SEQUENCE: 20
ccgaactact ctgacaggaa tacacg                                          26

<210> SEQ ID NO 21
<211> LENGTH: 507
<212> TYPE: DNA
<213> ORGANISM: Artificial Sequence
<220> FEATURE:
<223> OTHER INFORMATION: Description of Artificial Sequence: Synthetic
      nucleotide sequence coding mutein HbgA
<220> FEATURE:
<221> NAME/KEY: CDS
<222> LOCATION: (1)..(507)
<223> OTHER INFORMATION: mutein HbgA

<400> SEQUENCE: 21 caa gca ttt cat ctt ggg aag tgc ccc aat cct ccg gtg cag gag aat      48
Gln Ala Phe His Leu Gly Lys Cys Pro Asn Pro Pro Val Gln Glu Asn
1               5                   10                  15 ttt gac gtg aat aag tat cca gga aga tgg tac gaa att gag aag atc      96
Phe Asp Val Asn Lys Tyr Pro Gly Arg Trp Tyr Glu Ile Glu Lys Ile
            20                  25                  30 cca cag ttt gtt tgg atg gga cgc tgc atc cag gcc aac tac tca cta     144
Pro Gln Phe Val Trp Met Gly Arg Cys Ile Gln Ala Asn Tyr Ser Leu
        35                  40                  45 atg gaa aac gga aag atc aaa gtg tta aac cag ttt ttg cgg att acg     192
Met Glu Asn Gly Lys Ile Lys Val Leu Asn Gln Phe Leu Arg Ile Thr
    50                  55                  60 ctt gat gtg tgg caa atc gaa ggt gaa gcc acc cca gtt aac ctc act     240
Leu Asp Val Trp Gln Ile Glu Gly Glu Ala Thr Pro Val Asn Leu Thr
65                  70                  75                  80 gag cct gcc aag ctc gag gtt aag gag ggt ttg ggg gat cca tcg gca     288
Glu Pro Ala Lys Leu Glu Val Lys Glu Gly Leu Gly Asp Pro Ser Ala
                85                  90                  95 ccg tac tgg atc ctg gcc acc gac tat gag aac tat gcc ctc gtg tat     336
Pro Tyr Trp Ile Leu Ala Thr Asp Tyr Glu Asn Tyr Ala Leu Val Tyr
            100                 105                 110 tcc tgt gag agt ttt ctt tgg ttg ttt cac tgg gat ttt gct tgg atc     384
Ser Cys Glu Ser Phe Leu Trp Leu Phe His Trp Asp Phe Ala Trp Ile
        115                 120                 125 ttg gcc aga aac gtg gct ctc cct cca gaa aca gtg gac tct cta aaa     432
Leu Ala Arg Asn Val Ala Leu Pro Pro Glu Thr Val Asp Ser Leu Lys
    130                 135                 140 aat atc ctg act tct aat aac att gat gtc aag aaa atg acg gtc aca     480
Asn Ile Leu Thr Ser Asn Asn Ile Asp Val Lys Lys Met Thr Val Thr
145                 150                 155                 160 gac cag gtg aac tgc ccc aag ctc agc                                 507
Asp Gln Val Asn Cys Pro Lys Leu Ser
                165

<210> SEQ ID NO 22
<211> LENGTH: 599
<212> TYPE: PRT
<213> ORGANISM: Artificial Sequence
<220> FEATURE:
<223> OTHER INFORMATION: Description of Artificial Sequence: Synthetic
      Protein Construct
<220> FEATURE:
<221> NAME/KEY: SIGNAL
<222> LOCATION: (-21)..(-1)
```

-continued

```
<220> FEATURE:
<221> NAME/KEY: CHAIN
<222> LOCATION: (1)..(578)
<223> OTHER INFORMATION: fusion protein of apolipoprotein D,
      Strep-tag II and fragment of phage coat protein pIII
<220> FEATURE:
<221> NAME/KEY: MISC_FEATURE
<222> LOCATION: (1)..(169)
<223> OTHER INFORMATION: mature ApoD
<220> FEATURE:
<221> NAME/KEY: MISC_FEATURE
<222> LOCATION: (170)..(173)
<223> OTHER INFORMATION: linker peptide Ala-Gly-Gly-Ala
<220> FEATURE:
<221> NAME/KEY: MISC_FEATURE
<222> LOCATION: (174)
<223> OTHER INFORMATION: amber stop codon
<220> FEATURE:
<221> NAME/KEY: MISC_FEATURE
<222> LOCATION: (175)..(578)
<223> OTHER INFORMATION: amino acids 3-406 of coat protein pIII
```

<400> SEQUENCE: 22

Met Lys Lys Thr Ala Ile Ala Ile Ala Val Ala Leu Ala Gly Phe Ala
    -20              -15                 -10

Thr Val Ala Gln Ala Gln Ala Phe His Leu Gly Lys Cys Pro Asn Pro
-5           -1  1           5                       10

Pro Val Gln Glu Asn Phe Asp Val Asn Lys Tyr Pro Gly Arg Trp Tyr
            15                  20                  25

Glu Ile Glu Lys Ile Pro Thr Thr Phe Glu Asn Gly Arg Cys Ile Gln
            30                  35                  40

Ala Asn Tyr Ser Leu Met Glu Asn Gly Lys Ile Lys Val Leu Asn Gln
            45                  50                  55

Glu Leu Arg Ala Asp Gly Thr Val Asn Gln Ile Glu Gly Glu Ala Thr
60              65                  70                      75

Pro Val Asn Leu Thr Glu Pro Ala Lys Leu Glu Val Lys Phe Ser Trp
            80                  85                      90

Phe Met Pro Ser Ala Pro Tyr Trp Ile Leu Ala Thr Asp Tyr Glu Asn
            95                  100                     105

Tyr Ala Leu Val Tyr Ser Cys Thr Ser Ile Ile Gln Leu Phe His Val
            110                 115                     120

Asp Phe Ala Trp Ile Leu Ala Arg Asn Val Ala Leu Pro Pro Glu Thr
            125                 130                     135

Val Asp Ser Leu Lys Asn Ile Leu Thr Ser Asn Asn Ile Asp Val Lys
140                 145                 150                 155

Lys Met Thr Val Thr Asp Gln Val Asn Cys Pro Lys Leu Ser Ala Gly
                160                 165                 170

Gly Ala Gln Thr Val Glu Ser Cys Leu Ala Lys Pro His Thr Glu Asn
            175                 180                 185

Ser Phe Thr Asn Val Trp Lys Asp Lys Thr Leu Asp Arg Tyr Ala
            190                 195                 200

Asn Tyr Glu Gly Cys Leu Trp Asn Ala Thr Gly Val Val Cys Thr
            205                 210                 215

Gly Asp Glu Thr Gln Cys Tyr Gly Thr Trp Val Pro Ile Gly Leu Ala
220                 225                 230                 235

Ile Pro Glu Asn Glu Gly Gly Gly Ser Glu Gly Gly Ser Glu Gly
                240                 245                 250

Gly Gly Ser Glu Gly Gly Gly Thr Lys Pro Pro Glu Tyr Gly Asp Thr
            255                 260                 265

Pro Ile Pro Gly Tyr Thr Tyr Ile Asn Pro Leu Asp Gly Thr Tyr Pro

```
                270                 275                 280
Pro Gly Thr Glu Gln Asn Pro Ala Asn Pro Asn Pro Ser Leu Glu Glu
    285                 290                 295

Ser Gln Pro Leu Asn Thr Phe Met Phe Gln Asn Asn Arg Phe Arg Asn
300                 305                 310                 315

Arg Gln Gly Ala Leu Thr Val Tyr Thr Gly Thr Val Thr Gln Gly Thr
                320                 325                 330

Asp Pro Val Lys Thr Tyr Tyr Gln Tyr Thr Pro Val Ser Ser Lys Ala
                335                 340                 345

Met Tyr Asp Ala Tyr Trp Asn Gly Lys Phe Arg Asp Cys Ala Phe His
                350                 355                 360

Ser Gly Phe Asn Glu Asp Pro Phe Val Cys Glu Tyr Gln Gly Gln Ser
365                 370                 375

Ser Asp Leu Pro Gln Pro Pro Val Asn Ala Gly Gly Ser Gly Gly
380                 385                 390                 395

Gly Ser Gly Gly Gly Ser Glu Gly Gly Ser Glu Gly Gly Ser
                400                 405                 410

Glu Gly Gly Gly Ser Glu Gly Gly Ser Gly Gly Ser Gly Ser
                415                 420                 425

Gly Asp Phe Asp Tyr Glu Lys Met Ala Asn Ala Asn Lys Gly Ala Met
                430                 435                 440

Thr Glu Asn Ala Asp Glu Asn Ala Leu Gln Ser Asp Ala Lys Gly Lys
    445                 450                 455

Leu Asp Ser Val Ala Thr Asp Tyr Gly Ala Ala Ile Asp Gly Phe Ile
460                 465                 470                 475

Gly Asp Val Ser Gly Leu Ala Asn Gly Asn Gly Ala Thr Gly Asp Phe
                480                 485                 490

Ala Gly Ser Asn Ser Gln Met Ala Gln Val Gly Asp Gly Asp Asn Ser
                495                 500                 505

Pro Leu Met Asn Asn Phe Arg Gln Tyr Leu Pro Ser Leu Pro Gln Ser
            510                 515                 520

Val Glu Cys Arg Pro Phe Val Phe Gly Ala Gly Lys Pro Tyr Glu Phe
    525                 530                 535

Ser Ile Asp Cys Asp Lys Ile Asn Leu Phe Arg Gly Val Phe Ala Phe
540                 545                 550                 555

Leu Leu Tyr Val Ala Thr Phe Met Tyr Val Phe Ser Thr Phe Ala Asn
                560                 565                 570

Ile Leu Arg Asn Lys Glu Ser
            575

<210> SEQ ID NO 23
<211> LENGTH: 199
<212> TYPE: PRT
<213> ORGANISM: Artificial Sequence
<220> FEATURE:
<223> OTHER INFORMATION: Description of Artificial Sequence: Synthetic
      Protein Construct
<220> FEATURE:
<221> NAME/KEY: SIGNAL
<222> LOCATION: (-21)..(-1)
<220> FEATURE:
<221> NAME/KEY: CHAIN
<222> LOCATION: (1)..(178)
<223> OTHER INFORMATION: fusion protein of modified ApoD, Strep-tag II
<220> FEATURE:
<221> NAME/KEY: MISC_FEATURE
<222> LOCATION: (1)..(169)
<223> OTHER INFORMATION: mature ApoD
<220> FEATURE:
```

-continued

```
<221> NAME/KEY: MISC_FEATURE
<222> LOCATION: (170)..(178)
<223> OTHER INFORMATION: Strep-tag II affinity tag

<400> SEQUENCE: 23

Met Lys Lys Thr Ala Ile Ala Ile Ala Val Ala Leu Ala Gly Phe Ala
    -20                 -15                 -10

Thr Val Ala Gln Ala Gln Ala Phe His Leu Gly Lys Cys Pro Asn Pro
-5              -1   1               5                      10

Pro Val Gln Glu Asn Phe Asp Val Asn Lys Tyr Pro Gly Arg Trp Tyr
            15                  20              25

Glu Ile Glu Lys Ile Pro Thr Thr Phe Glu Asn Gly Arg Cys Ile Gln
            30                  35              40

Ala Asn Tyr Ser Leu Met Glu Asn Gly Lys Ile Lys Val Leu Asn Gln
45                  50                  55

Glu Leu Arg Ala Asp Gly Thr Val Asn Gln Ile Glu Gly Glu Ala Thr
60                  65                  70                  75

Pro Val Asn Leu Thr Glu Pro Ala Lys Leu Glu Val Lys Phe Ser Trp
                80                  85                  90

Phe Met Pro Ser Ala Pro Tyr Trp Ile Leu Ala Thr Asp Tyr Glu Asn
            95                  100                 105

Tyr Ala Leu Val Tyr Ser Cys Thr Ser Ile Ile Gln Leu Phe His Val
            110                 115                 120

Asp Phe Ala Trp Ile Leu Ala Arg Asn Val Ala Leu Pro Pro Glu Thr
            125                 130                 135

Val Asp Ser Leu Lys Asn Ile Leu Thr Ser Asn Asn Ile Asp Val Lys
140                 145                 150                 155

Lys Met Thr Val Thr Asp Gln Val Asn Cys Pro Lys Leu Ser Ala Trp
                160                 165                 170

Ser His Pro Gln Phe Glu Lys
            175

<210> SEQ ID NO 24
<211> LENGTH: 248
<212> TYPE: PRT
<213> ORGANISM: Artificial Sequence
<220> FEATURE:
<223> OTHER INFORMATION: Description of Artificial Sequence: Synthetic
      Protein Construct
<220> FEATURE:
<221> NAME/KEY: SIGNAL
<222> LOCATION: (-21)..(-1)
<220> FEATURE:
<221> NAME/KEY: CHAIN
<222> LOCATION: (1)..(227)
<223> OTHER INFORMATION: fusion protein of modified ApoD, Strep-tag II
      and albumin binding domain
<220> FEATURE:
<221> NAME/KEY: MISC_FEATURE
<222> LOCATION: (1)..(169)
<223> OTHER INFORMATION: mature ApoD
<220> FEATURE:
<221> NAME/KEY: MISC_FEATURE
<222> LOCATION: (170)..(178)
<223> OTHER INFORMATION: Strep-tag II affinity tag
<220> FEATURE:
<221> NAME/KEY: MISC_FEATURE
<222> LOCATION: (179)..(227)
<223> OTHER INFORMATION: albumin binding domain of Protein G

<400> SEQUENCE: 24

Met Lys Lys Thr Ala Ile Ala Ile Ala Val Ala Leu Ala Gly Phe Ala
    -20                 -15                 -10
```

```
Thr Val Ala Gln Ala Gln Ala Phe His Leu Gly Lys Cys Pro Asn Pro
 -5          -1   1             5                      10

Pro Val Gln Glu Asn Phe Asp Val Asn Lys Tyr Pro Gly Arg Trp Tyr
            15              20              25

Glu Ile Glu Lys Ile Pro Thr Thr Phe Glu Asn Gly Arg Cys Ile Gln
        30              35              40

Ala Asn Tyr Ser Leu Met Glu Asn Gly Lys Ile Lys Val Leu Asn Gln
45              50              55

Glu Leu Arg Ala Asp Gly Thr Val Asn Gln Ile Glu Gly Glu Ala Thr
60              65              70              75

Pro Val Asn Leu Thr Glu Pro Ala Lys Leu Glu Val Lys Phe Ser Trp
                80              85              90

Phe Met Pro Ser Ala Pro Tyr Trp Ile Leu Ala Thr Asp Tyr Glu Asn
            95              100             105

Tyr Ala Leu Val Tyr Ser Cys Thr Ser Ile Ile Gln Leu Phe His Val
            110             115             120

Asp Phe Ala Trp Ile Leu Ala Arg Asn Val Ala Leu Pro Pro Glu Thr
            125             130             135

Val Asp Ser Leu Lys Asn Ile Leu Thr Ser Asn Asn Ile Asp Val Lys
140             145             150             155

Lys Met Thr Val Thr Asp Gln Val Asn Cys Pro Lys Leu Ser Ala Trp
            160             165             170

Ser His Pro Gln Phe Glu Lys Pro Ala Ser Leu Ala Glu Ala Lys Val
            175             180             185

Leu Ala Asn Arg Glu Leu Asp Lys Tyr Gly Val Ser Asp Tyr Tyr Lys
            190             195             200

Asn Leu Ile Asn Asn Ala Lys Thr Val Glu Gly Val Lys Ala Leu Ile
            205             210             215

Asp Glu Ile Leu Ala Ala Leu Pro
220              225
```

<210> SEQ ID NO 25
<211> LENGTH: 169
<212> TYPE: PRT
<213> ORGANISM: Artificial Sequence
<220> FEATURE:
<223> OTHER INFORMATION: Description of Artificial Sequence: Synthetic
      Protein Construct

<400> SEQUENCE: 25

```
Gln Ala Phe His Leu Gly Lys Cys Pro Asn Pro Val Gln Glu Asn
1               5                   10                  15

Phe Asp Val Asn Lys Tyr Pro Gly Arg Trp Tyr Glu Ile Glu Lys Ile
            20              25              30

Pro Gln Phe Val Trp Met Gly Arg Cys Ile Gln Ala Asn Tyr Ser Leu
        35              40              45

Met Glu Asn Gly Lys Ile Lys Val Leu Asn Gln Phe Leu Arg Ile Thr
        50              55              60

Leu Asp Val Trp Gln Ile Glu Gly Glu Ala Thr Pro Val Asn Leu Thr
65              70              75              80

Glu Pro Ala Lys Leu Glu Val Lys Glu Gly Leu Gly Asp Pro Ser Ala
            85              90              95

Pro Tyr Trp Ile Leu Ala Thr Asp Tyr Glu Asn Tyr Ala Leu Val Tyr
            100             105             110

Ser Cys Glu Ser Phe Leu Trp Leu Phe His Trp Asp Phe Ala Trp Ile
            115             120             125
```

```
Leu Ala Arg Asn Val Ala Leu Pro Pro Glu Thr Val Asp Ser Leu Lys
    130                 135                 140

Asn Ile Leu Thr Ser Asn Asn Ile Asp Val Lys Lys Met Thr Val Thr
145                 150                 155                 160

Asp Gln Val Asn Cys Pro Lys Leu Ser
                165
```